United States Patent
Watanabe et al.

(10) Patent No.: US 7,268,250 B2
(45) Date of Patent: Sep. 11, 2007

(54) PROCESS FOR PRODUCING OPTICALLY ACTIVE COMPOUND

(75) Inventors: Masahito Watanabe, Soka (JP); Kunihiko Murata, Soka (JP); Takao Ikariya, Tokyo (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 165 days.

(21) Appl. No.: 10/749,806

(22) Filed: Dec. 31, 2003

(65) Prior Publication Data

US 2004/0176616 A1    Sep. 9, 2004

(30) Foreign Application Priority Data

Jan. 17, 2003  (JP) ............................. 2003-009786
Mar. 17, 2003  (JP) ............................. 2003-071368

(51) Int. Cl.
    *C07C 67/36*   (2006.01)
(52) U.S. Cl. .................. 560/114; 560/174; 560/175; 502/171
(58) Field of Classification Search ............... 560/114, 560/174, 175; 502/171
    See application file for complete search history.

(56) References Cited

FOREIGN PATENT DOCUMENTS

| JP | 07-265709 | 10/1995 |
|----|-----------|---------|
| JP | 8291178 | 5/1996 |
| JP | 08-319258 | 12/1996 |
| JP | 10-130286 | 5/1998 |
| JP | 10 130289 | 5/1998 |
| JP | 11-240865 | 9/1999 |
| JP | 2001-031682 | 2/2001 |
| JP | 2001-252567 | 9/2001 |
| JP | 2002-069076 | 3/2002 |

OTHER PUBLICATIONS

Database accession No. 2003:634256.

Suzuki et al., "Catalytic asymmetric Michael reactions using a chiral rhodium complex"; 2001; Tetrahedron: Asymmetry, vol. 12; 1077-1081.

Sasai et al., "Catalytic Asymmetric Michael Reactions Promoted by the La-Na-BINOL Complex (LSB). Enantioface Selection on Michael Donors"; 1996; Tetrahedron Letters, vol. 37(31); 5561-5564.

Prabagaran et al., "Asymmetric Michael addition reactions using a chiral La-Na aminodiolate catalyst", 2002; Tetrahedron Asymmetry, vol. 13; 1053-1058.

Kumaraswamy et al., "Calcium-BINOL: a novel and efficient catalyst for asymmetric Michael reactions", 2001; Tetrahedron Letters, vol. 42; 8515-8517.

Noyori et al., "Asymmetric Transfer Hydrogenation Catalyzed by Chiral Ruthenium Complexes", 1997; Acc. Chem. Res., vol. 30(2); 97-102.

Haack et. al., "The Catalyst Precursor, Catalyst, and Intermediate in the Rull-Promoted Asymmetric Hydrogen Transfer between Alcohols and Ketones", 1997; Angew. Chem. Int. Ed. Engl., vol. 36(3);285-288.

Watanabe et al., "Enantioselective Michael Reaction Catalyzed by Well-Defined Chiral Ru Amido Complexes: Isolation and Characterization of the Catalyst Intermediate, Ru Malonato Complex Having a Metal—Carbon Bond", 2003; J. Am. Chem. Soc., vol. 125(25);7508-7509.

Karl-Josef Haack, Shohei Hashiguchi, Akio Fujii, Takao Ikariya, Ryoji Noyori. The Catalyst Precursor, Catalyst, and Intermediate in the $Ru^{II}$-Promoted Asymmetric Hydrogen Transfer between Alcohols and Ketones. Angew. Chem. Int. Ed. Engl. 1997, 36, No. 3. pp. 285-288.

Kunihiko Murata, Takao Ikariya, and Ryoji Noyori. New Chiral Phodium and Iridium Complexes with Chiral Diamine Ligands for Asymmetric Transfer Hydrogenation of Aromatic Ketones. J. Org. Chem. 1999, 64, 2186-2187.

*Primary Examiner*—Rebecca Anderson
*Assistant Examiner*—Robert Shiao
(74) *Attorney, Agent, or Firm*—Peter F. Corless; Jeffrey D. Hsi; Edwards Angell Palmer & Dodge LLP

(57) ABSTRACT

A highly efficient process is provided for producing an optically active compound having high optical purity by an asymmetric reaction using as a catalyst a transition metal complex having an optically active nitrogen-containing compound as an asymmetric ligand.

6 Claims, No Drawings

PROCESS FOR PRODUCING OPTICALLY ACTIVE COMPOUND

BACKGROUND OF THE INVENTION

1. Technical Field to Which the Invention Pertains

The present invention relates to an efficient process for producing an optically active compound having high optical purity by using, as a catalyst in an asymmetric Michael reaction, a transition metal complex having an optically active nitrogen-containing compound as an asymmetric ligand.

2. Prior Art

Optically active compounds obtained by an asymmetric Michael reaction are useful as synthetic intermediates for pharmaceuticals, etc. For example, an optically active ketone obtained by an asymmetric Michael reaction of an enone can be used as a synthetic intermediate for a prostaglandin, etc. With regard to a process for synthesizing these optically active ketones, various processes have been developed, and known examples of asymmetric Michael reactions using an asymmetric catalyst are as follows. For example, there are asymmetric lanthanoid complex catalysts (ref. JP, A, 7-265709, JP, A, 8-291178, JP, A, 11-240865, JP, A, 2001-31682, or JP, A, 2002-69076), and asymmetric aluminum complex catalysts (ref. JP, A, 2001-31682 or JP, A, 8-319258). Furthermore, asymmetric rhodium complexes (ref. JP, A, 10-130286) and asymmetric hafnium, titanium, zirconium complex catalysts (ref. JP, A, 2001-252567) have been reported.

The asymmetric lanthanoid catalysts, which have a lanthanoid as a center metal, have a different metal such as lithium in the catalyst molecule, and it is thought that the lanthanoid and lithium activate a Michael donor and a Michael acceptor respectively. It is therefore necessary to have two different types of metal in the molecule, and it is thus necessary to design an asymmetric metal complex having a complicated structure.

These processes cannot therefore be always said to be highly practical since it might be difficult to prepare the catalyst, the catalyst might have a stability problem, it might be necessary to use a large amount of catalyst, or it might be necessary to carry out the reaction at low temperature or for a long time.

The present invention has been achieved under the above-mentioned circumstances, and it is an object thereof to provide an efficient process for producing a Michael addition product having high optical purity by an asymmetric Michael reaction using a catalytic amount of an asymmetric source under mild conditions.

SUMMARY OF THE INVENTION

As a result of an intensive investigation by the present inventors, it has been found that a Michael addition product having high optical purity can be obtained highly efficiently by using, in an asymmetric Michael reaction, an asymmetric metal complex that is obtained by reacting an optically active nitrogen-containing compound, a complex of a metal of group VIII of the periodic table, and a base, and the present invention, which is a novel, very efficient catalytic system, has thus been accomplished.

That is, the gist of the present invention is to provide a process for producing an optically active compound represented by general formula (C)

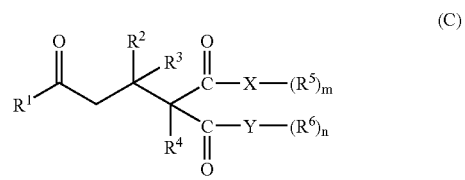

(in the formula, $R^1$ denotes an aromatic monocyclic or aromatic polycyclic hydrocarbon group, which may have a substituent, a saturated or unsaturated aliphatic hydrocarbon group or alicyclic hydrocarbon group, which may have a substituent, a heteromonocyclic or heteropolycyclic group, which may have a substituent, or a hydrogen atom, an alkoxy group, or an amino group; $R^2$ and $R^3$ independently denote a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a heteromonocyclic or heteropolycyclic group, which may have a substituent, and $R^1$ and $R^2$, $R^1$ and $R^3$, or $R^2$ and $R^3$ may be bonded to each other to form a ring; $R^4$ denotes a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a heteromonocyclic or heteropolycyclic group, which may have a substituent; $R^5$ and $R^6$ independently denote a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a straight-chain or branched C1 to C20 alkoxy group, and $R^4$ and $R^5$, $R^4$ and $R^6$, or $R^5$ and $R^6$ may be bonded to each other to form a ring; X and Y independently denote a single bond, an oxygen atom, a sulfur atom, a nitrogen atom, or a phosphorus atom; and m and n are independently 1 or 2; when X and/or Y is a single bond, an oxygen atom, or a sulfur atom, m and/or n is 1, and when X and/or Y is a nitrogen atom or a phosphorus atom, m and/or n is 2) by reacting a compound represented by general formula (A)

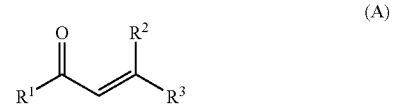

(in the formula, $R^1$, $R^2$, and $R^3$ have the same meaning as above) and a compound represented by general formula (B)

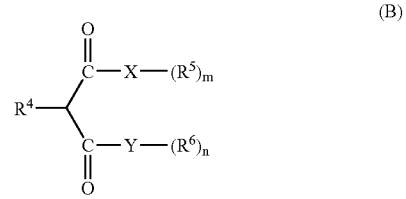

(in the formula, $R^4$, $R^5$, $R^6$, X, Y, m, and n have the same meaning as above) with an asymmetric metal complex obtained from an optically active nitrogen-containing compound and a complex of a metal of group VIII of the periodic table.

Furthermore, the present invention relates to the above-mentioned process for producing an optically active compound, wherein X and Y of the above-mentioned compound (B) are both oxygen atoms.

Moreover, the present invention relates to the above-mentioned process for producing an optically active compound, wherein X of the above-mentioned compound (B) is an oxygen atom and Y is a single bond, or X is a single bond and Y is an oxygen atom.

Furthermore, the present invention relates to the above-mentioned process for producing an optically active compound, wherein the optically active nitrogen-containing compound has a structure represented by general formula (D)

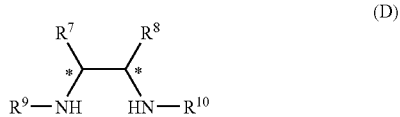

(in the formula, $R^7$ and $R^8$ independently denote an aromatic monocyclic or aromatic polycyclic hydrocarbon group, which may have a substituent, a saturated or unsaturated aliphatic hydrocarbon group or alicyclic hydrocarbon group, which may have a substituent, or a heteromonocyclic or heteropolycyclic group, which may have a substituent, and $R^7$ and $R^8$ may be bonded to each other to form a ring; $R^9$ denotes a hydrogen atom or an alkyl group; $R^{10}$ denotes an acyl group, a carbamoyl group, a thioacyl group, a thiocarbamoyl group, an alkylsulfonyl group, or an arylsulfonyl group; and * denotes an asymmetric carbon atom).

Moreover, the present invention relates to the above-mentioned process for producing an optically active compound, wherein in the optically active nitrogen-containing compound represented by general formula (D), $R^{10}$ has a structure represented by

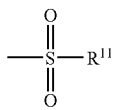

(in the formula, $R^{11}$ denotes an alkyl group or aryl group, which may have a substituent).

Furthermore, the present invention relates to the above-mentioned process for producing an optically active compound, wherein in the optically active nitrogen-containing compound represented by general formula (D), $R^7$ has a structure represented by

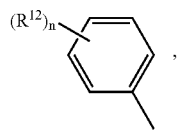

$R^8$ has a structure represented by

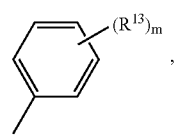

and $R^{10}$ has a structure represented by

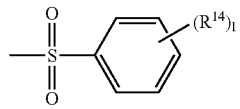

(in the formulae, $R^{12}$, $R^{13}$ and $R^{14}$ independently denote a hydrogen atom, an alkyl group, a halogen atom, or an alkoxy group, and l, m, and n independently denote an integer of 1 to 5).

Moreover, the present invention relates to the above-mentioned process for producing an optically active compound, wherein the complex of a metal of group VIII of the periodic table is a ruthenium compound.

Furthermore, the present invention relates to the above-mentioned process for producing an optically active compound, wherein the asymmetric metal complex is an asymmetric ruthenium amido complex represented by general formula (E)

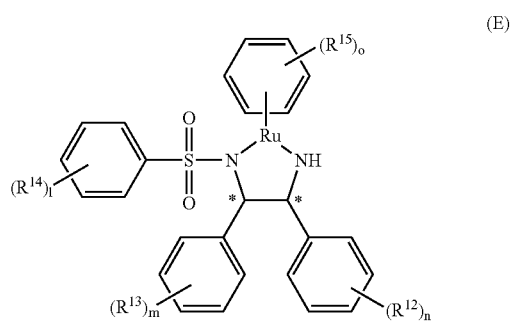

(in the formula, $R^{12}$, $R^{13}$, $R^{14}$, l, m and n have the same meaning as above, $R^{15}$ denotes a methyl group, an ethyl group, a propyl group, or an isopropyl group, o denotes an integer of 0 to 6, and * denotes an asymmetric carbon atom).

Moreover, the present invention relates to the above-mentioned process for producing an optically active compound, wherein the asymmetric metal complex is an asymmetric ruthenium hydrido complex represented by general formula (F)

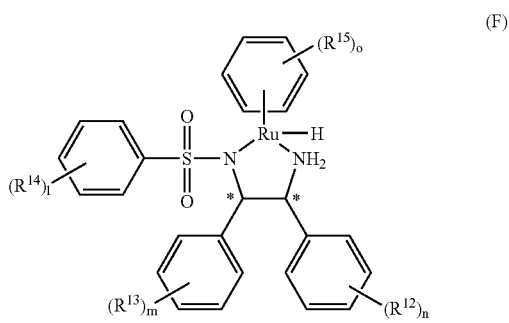

(in the formula, $R^{12}$, $R^{13}$, $R^{14}$, $R^{15}$, l, m, n and o have the same meaning as above, and * denotes an asymmetric carbon atom).

This invention exhibits very high performance by using an asymmetric metal catalyst having an optically active nitrogen-containing compound as a ligand even though only a single metal of group VIII of the periodic table is contained in the catalyst.

With regard to the optically active nitrogen-containing ligand, from the viewpoint of strong bonding to the metal by σ-bonding and maintaining an appropriate structure of a catalytically active species in terms of the organometallic complex chemistry, a sulfonamide group or carboxamide group structure is preferable. That is, by the use of an asymmetric metal complex obtained from a metal of group VIII of the periodic table and an optically active diamine ligand having a sulfonamide group or a carboxamide group, a very effective, novel catalyst, which has a different reaction mechanism from that of a conventional catalyst for an asymmetric Michael reaction, has been developed.

MODES FOR CARRYING OUT THE INVENTION

The present invention is explained in detail below. A compound used as a starting material in the present invention is represented by the above-mentioned general formula (A).

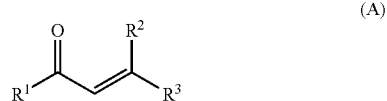

(A)

In the formula (A), $R^1$ denotes an aromatic monocyclic or aromatic polycyclic hydrocarbon group, which may have a substituent, a saturated or unsaturated aliphatic hydrocarbon group or alicyclic hydrocarbon group, which may have a substituent, a heteromonocyclic or heteropolycyclic group, which may have a substituent, or a hydrogen atom, an alkoxy group, or an amino group. In the formula, $R^2$ and $R^3$ independently denote a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a heteromonocyclic or heteropolycyclic group which may have a substituent.

Making $R^2$ and $R^3$ different from each other enables an optically active compound having an asymmetric carbon at the β position to the carbonyl to be produced.

In general formula (A), $R^1$, $R^2$, and $R^3$ are independent from each other, and in the definition of the groups, the terms have the meanings below.

Specific examples of the aromatic monocyclic or aromatic polycyclic hydrocarbon group include phenyl, 2-methylphenyl, 2-ethylphenyl, 2-isopropylphenyl, 2-tert-butylphenyl, 2-methoxyphenyl, 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, cumenyl, mesityl, xylyl, 1-naphthyl, 2-naphthyl, anthryl, phenathryl, and indenyl groups.

Specific examples of the heteromonocyclic or heteropolycyclic group include thienyl, furyl, pyranyl, pyrrolyl, imidazolyl, pyrazolyl, oxazolyl, isooxazolyl, triazolyl, thiazolyl, isothiazolyl, pyridyl, pyridazyl, pyrazinyl, benzoimidazolyl, benzopyrazolyl, benzothiazolyl, quinolyl, anthranyl, indolyl, and phenanthrolyl groups.

The aliphatic hydrocarbon group is a straight-chain or branched alkyl, alkenyl, or alkynyl group, each of which may be substituted with an aromatic hydrocarbon group or a heterocyclic group.

Examples of the alkyl group include alkyl groups having 1 to 20 carbons such as methyl, ethyl, n-propyl, isopropyl, butyl, sec-butyl, tert-butyl, pentyl, isopentyl, neopentyl, tert-pentyl, hexyl, heptyl, octyl, nonyl, decyl, and dodecyl groups. Examples of the alkenyl group include alkenyl groups having 2 to 20 carbons such as vinyl, 1-propenyl, 2-propenyl, 1-butenyl, 1-isopropenyl, 2-butenyl, 3-butenyl, 1,3-butadienyl, 1-pentenyl, 2-pentenyl, and 3-pentenyl groups. Examples of the alkynyl group include alkynyl groups having 2 to 20 carbons such as ethynyl, 1-propynyl, and phenylethynyl groups.

The alicyclic hydrocarbon group denotes a cycloalkyl group, which may be substituted with an aromatic hydrocarbon or heterocyclic group, and specific examples thereof include cycloalkyl groups having 3 to 8 carbons such as cyclopropyl, cyclobutyl, cyclopentyl, and cyclohexyl groups.

Specific examples of the alkoxy group include alkoxy groups having 1 to 20 carbons such as methoxy, ethoxy, propoxy, and butoxy groups as well as those including an aromatic ring such as a phenoxy group.

Specific examples of the amino group include amino, methylamino, dimethylamino, ethylamino, and diethylamino groups.

Specific examples of the substituent that is bonded to the above-mentioned aromatic hydrocarbon group, heterocyclic group, aliphatic hydrocarbon group or alicyclic hydrocarbon group include a halogen atom such as fluorine, chlorine, bromine, or iodine, a halogen atom-containing hydrocarbon group such as a trifluoromethyl group, an oxygen atom-containing substituent such as a hydroxyl, alkoxy, acyl, alkoxycarbonyl, or carboxyl group, a nitrogen atom-containing substituent such as an amino, alkylamino, nitro, cyano, or azido group, a silicon-containing substituent such as a trimethylsilyl or hydrosilyl group, a sulfur atom-containing substituent such as a mercapto or alkylthio group, and a phosphorus atom-containing substituent such as a phosphoryl or triphenylphosphinyl group.

The substituent may contain a transition metal element, and specific examples thereof include an iron-containing substituent such as a ferrocenyl group. Furthermore, $R^1$ and $R^2$, $R^1$ and $R^3$, or $R^2$ and $R^3$ may be bonded to each other to form a ring.

Specific examples of the compound represented by general formula (A) include compounds shown in Compound Group 1, and particularly highly applicable are 2-cyclopentenone (1 of Compound Group 1), 4,4-dimethyl-2-cyclopentenone (2 of Compound Group 1), and 2-cyclohexenone (4 of Compound Group 1). The compounds represented by general formula (A) are not limited to the compounds of Compound Group 1.

Compound group 1

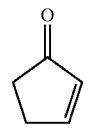

1

-continued

-continued

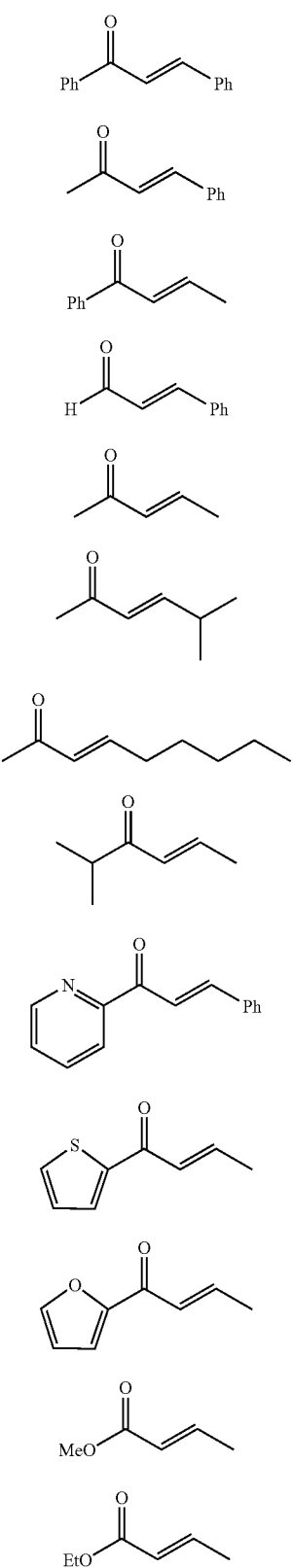

The compound that is a Michael donor starting material of the present invention is represented by general formula (B).

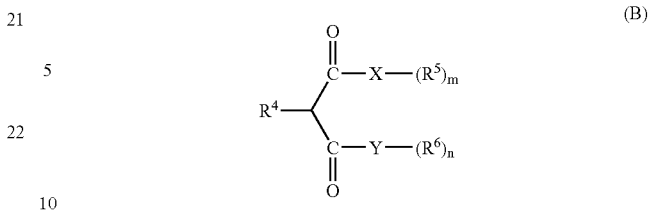

In general formula (B), $R^4$ is a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a heteromonocyclic or heteropolycyclic group, which may have a substituent, and $R^5$ and $R^6$ independently denote a hydrogen atom, an aromatic monocyclic or aromatic polycyclic hydrocarbon group, which may have a substituent, a saturated or unsaturated aliphatic hydrocarbon group or alicyclic hydrocarbon group, which may have a substituent, or a straight-chain or branched C1 to C20 alkoxy group. Furthermore, $R^4$ and $R^5$, $R^4$ and $R^6$, or $R^5$ and $R^6$ may be bonded to each other to form a ring. X and Y independently denote a single bond, an oxygen atom, a sulfur atom, a nitrogen atom, or a phosphorus atom, and m and n are independently 1 or 2. When X and/or Y is a single bond, an oxygen atom, or a sulfur atom, m and/or n is 1, and when X and/or Y is a nitrogen atom or a phosphorus atom, m or n is 2.

In general formula (B), $R^4$, $R^5$, and $R^6$ are independent from each other, but in the definition of the groups the terms have the above meanings.

Specific examples of the compound represented by general formula (B) include compounds shown in Compound Group 2, and particularly highly applicable are dimethyl malonate (1 of Compound Group 2), diethyl malonate (2 of Compound Group 2), and methyl acetoacetate (10 of Compound Group 2). In addition, the compounds represented by general formula (B) are not limited to the compounds of Compound Group 2, and the asymmetric carbon can be a carbon resulting from a new bond in a combination where —X—(R⁵)$_m$ and —Y—(R⁶)$_n$ are different in general formula (B) (e.g., 8 to 13 of Compound Group 2).

Compound Group 2

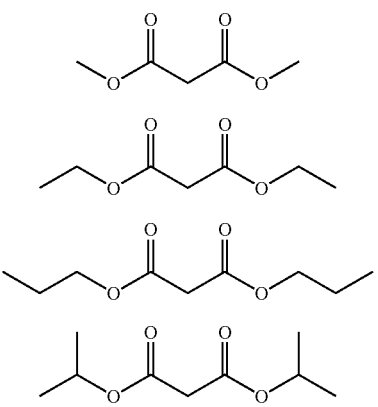

-continued

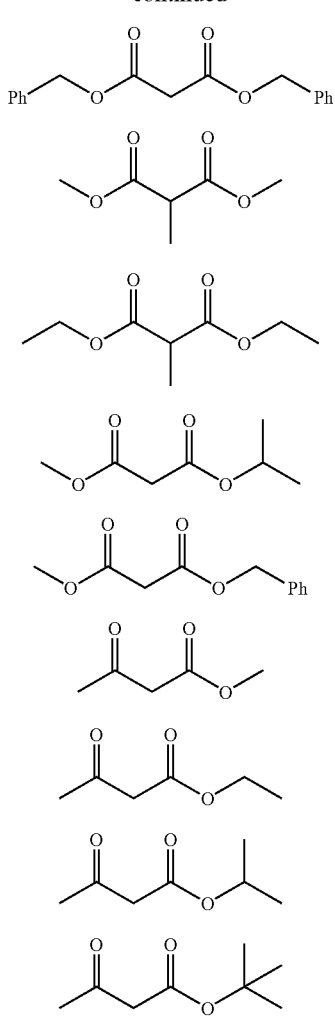

5
6
7
8
9
10
11
12
13

The optically active nitrogen-containing compound, which forms the catalyst used in the present invention, is a diamine derivative represented by general formula (D).

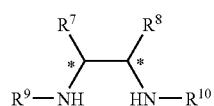

(D)

In general formula (D), $R^7$ and $R^8$ denote an alkyl group, for example, a straight-chain or branched alkyl group having 1 to 6 carbons such as a methyl, ethyl, n-propyl, isopropyl, butyl, sec-butyl, tert-butyl, pentyl, isopentyl, neopentyl, tert-pentyl, or hexyl group; preferably an aryl group such as, for example, a phenyl, naphthyl, 4-methylphenyl, 3,5-dimethylphenyl, or 4-methoxyphenyl group; or a heterocyclic group such as, for example, a furyl or pyridyl group. Alternatively, $R^7$ and $R^8$ may together form a tetramethylene group (forming a cyclohexane ring). These groups may be further substituted, and the substituent is one group or two or more groups selected from a lower alkyl group such as a methyl, ethyl, n-propyl, or isopropyl group, a lower alkoxy group such as a methoxy or ethoxy group, and a halogen atom such as a chlorine atom, a bromine atom, or a fluorine atom. $R^7$ and $R^8$ are each preferably a phenyl group or a phenyl group having a substituent, or a tetramethylene group in which $R^7$ and $R^8$ are bonded to each other, etc.

$R^9$ denotes a hydrogen atom or a lower alkyl group, for example, a straight-chain or branched alkyl group having 1 to 6 carbons such as a methyl, ethyl, n-propyl, or isopropyl group.

$R^{10}$ denotes an acyl group such as, for example, an acetyl, propionyl, or benzoyl group; a carbamoyl group such as, for example, an N-methylcarbamoyl or N-phenylcarbamoyl group; a thioacyl group such as, for example, a thioacetyl, thiopropionyl, or thiobenzoyl group; a thiocarbamoyl group such as, for example, an N-methylthiocarbamoyl or N-phenylthiocarbamoyl group; or an alkylsulfonyl group or an arylsulfonyl group, for example, an alkylsulfonyl or arylsulfonyl group having 1 to 20 carbons such as a methanesulfonyl, ethanesulfonyl, trifluoromethanesulfonyl, benzenesulfonyl, 2,4,6-trimethylsulfonyl, 2,4,6-triisopropylbenzenesulfonyl, 4-methoxybenzenesulfonyl, 4-chlorobenzenesulfonyl, or p-toluenesulfonyl group, which may have a substituent. A preferred combination of $R^9$ and $R^{10}$ is one in which $R^9$ is hydrogen and $R^{10}$ is an alkylsulfonyl or arylsulfonyl group and, in particular, $R^{10}$ is a methanesulfonyl or p-toluenesulfonyl group.

The optically active nitrogen-containing compound represented by general formula (D) is preferably a diamine derivative in which $R^{10}$ is represented by

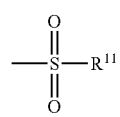

[Chem. 26]

(in the formula, $R^{11}$ denotes an alkyl or aryl group, which may have a substituent).

A more preferred optically active nitrogen-containing compound is a diamine derivative in which $R^7$ is

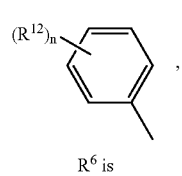

[Chem. 27]

$R^6$ is

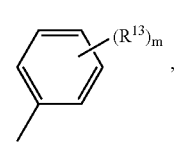

[Chem. 28]

and $R^{10}$ is

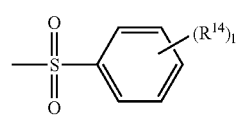

[Chem. 29]

(in the formulae, $R^{12}$ $R^{13}$ and $R^{14}$ independently denote a hydrogen atom, an alkyl group, a halogen atom, or an alkoxy group. l, m, and n independently denote an integer of 1 to 5).

Specific examples of $R^{11}$ to $R^{14}$ when they denote alkyl groups, aryl groups, halogen atoms, or alkoxy groups are the same as those cited for the $R^7$ and $R^8$ above. Specific examples of the asymmetric ligand represented by general formula (D) include 1,2-diphenylethylenediamine, N-methyl-1,2-diphenylethylenediamine, N-(p-toluenesulfonyl)-1,2-diphenylethylenediamine, N-methanesulfonyl-1,2-diphenylethylenediamine, N-methyl-N'-(p-toluenesulfonyl)-1,2-diphenylethylenediamine, N-methyl-N'-methanesulfonyl-1,2-diphenylethylenediamine, N-(p-methoxybenzenesulfonyl)-1,2-diphenylethylenediamine, N-(p-chlorobenzenesulfonyl)-1,2-diphenylethylenediamine, N-(3,5-dimethylbenzenesulfonyl)-1,2-diphenylethylenediamine, N-(3,5-di-i-propylbenzenesulfonyl)-1,2-diphenylethylenediamine, N-(2,4,6-trimethylbenzenesulfonyl)-1,2-diphenylethylenediamine, N-(2,4,6-tri-1-propylbenzenesulfonyl)-1,2-diphenylethylenediamine, N-trifluoromethanesulfonyl-1,2-diphenylethylenediamine, 1,2-cyclohexanediamine, N-methyl-1,2-cyclohexanediamine, N-(p-toluenesulfonyl)-1,2-cyclohexanediamine, N-methanesulfonyl-1,2-cyclohexanediamine, N-methyl-N'-(p-toluenesulfonyl)-1,2-cyclohexanediamine, N-methyl-N'-methanesulfonyl-1,2-cyclohexanediamine, N-(p-methoxybenzenesulfonyl)-1,2-cyclohexanediamine, N-(p-chlorobenzenesulfonyl)-1,2-cyclohexanediamine, N-(3,5-dimethylbenzenesulfonyl)-1,2-cyclohexanediamine, N-(3,5-di-i-propylbenzenesulfonyl)-1,2-cyclohexanediamine, N-(2,4,6-trimethylbenzenesulfonyl)-1,2-cyclohexanediamine, N-(2,4,6-tri-i-propylbenzenesulfonyl)-1,2-cyclohexanediamine, and N-trifluoromethanesulfonyl-1,2-cyclohexanediamine.

With regard to the metal species of a compound of a metal of group VIII of the periodic table, which is used in combination with these asymmetric ligands, ruthenium, rhodium, iridium, cobalt, iron, nickel, palladium, platinum, and osmium can be cited as examples, and among these ruthenium is preferable. Specific examples of the compound include $RuCl_3 \cdot 3H_2O$, $[RuCl_2(p\text{-cymene})]_2$, $[RuCl_2(benzene)]_2$, $[RuCl_2(methylbenzene)]_2$, $[RuCl_2(1,2\text{-dimethylbenzene})]_2$, $[RuCl_2(1,3\text{-dimethylbenzene})]_2$, $[RuCl_2(1,4\text{-dimethylbenzene})]2$, $[RuCl_2(mesitylene)]_2$, $[RuCl_2(1,2,3\text{-trimethylbenzene})]_2$, $[RuCl_2(1,2,4\text{-trimethylbenzene})]_2$, $[RuCl_2(1,2,3,4\text{-tetramethylbenzene})]_2$, $[RuCl_2(1,2,3,5\text{-tetramethylbenzene})]_2$, $[RuCl_2(1,2,4,5\text{-tetramethylbenzene})]_2$, $[RuCl_2(pentamethylbenzene)]_2$, $[RuCl_2(hexamethylbenzene)]_2$, $RuCl_2(PPh_3)_3$, $[RuCl_2(cod)]_2$, $[RuCl_2(CO)_3]_2$, $[Rh(cod)Cl]_2$, $[RhCl_2(pentamethylcyclopentadiene)]_2$, $[Ir(cod)Cl]_2$, $[IrCl_2 (pentamethylcyclopentadiene)]_2$, $CoCl_2$, $NiCl_2$, $NiCl_2(PPh_3)_2$, $PdCl_2$, $Pd(PPh_3)_4$, $PdCl_2(CH_3CN)_2$, $PdCl_2(PhCN)_2$, $PtCl_2(cod)$, and $Pt(PPh_3)_4$; and $[RuCl_2(p\text{-cymene})]_2$, $[RuCl_2(mesitylene)]_2$, $[RuCl_2(1,2,4,5\text{-tetramethylbenzene})]_2$, $[RuCl_2 (pentamethylbenzene)]_2$, and $[RuCl_2 (hexamethylbenzene)]_2$ are preferable. In the above-mentioned compounds, Ph denotes a phenyl group, and cod denotes cyclooctadiene. Cl in these compounds may be another halogen atom such as, for example, Br or I.

An asymmetric metal complex in which the optically active nitrogen-containing compound coordinates to the compound of a metal of group VIII of the periodic table and which is used as a catalyst can be obtained by reacting the compound of a metal of group VIII of the periodic table with the optically active nitrogen-containing compound and a base. Examples of the base used in this reaction include an alkali metal hydroxide such as lithium hydroxide, sodium hydroxide, or potassium hydroxide, an alkali metal alkoxide such as lithium methoxide, sodium methoxide, sodium ethoxide, or potassium isopropoxide, and an organic amine such as trimethylamine, triethylamine, or triisopropylamine. The base is preferably used in an excess amount relative to the halogen atom on the metal, for example, at a molar ratio of 1 to 100 times.

With regard to the asymmetric metal complex in which the optically active nitrogen-containing compound coordinates to the compound of a metal of group VIII of the periodic table and which is used as the catalyst, an amide complex and a hydrido complex can be cited. Specific examples of the ruthenium amide complex include

[(S,S)-N-(p-toluenesulfonyl)-1,2-diphenylethylenediamine] benzene ruthenium,

[(R,R)-N-(p-toluenesulfonyl)-1,2-diphenylethylenediamine]benzene ruthenium,

[(S,S)-N-(p-toluenesulfonyl)-1,2-diphenylethylenediamine] (methylbenzene) ruthenium,

[(R,R)-N-(p-toluenesulfonyl)-1,2-diphenylethylenediamine](methylbenzene) ruthenium,

[(S,S)-N-(p-toluenesulfonyl)-1,2-diphenylethylenediamine] (1,2-dimethylbenzene) ruthenium,

[(R,R)-N-(p-toluenesulfonyl)-1,2-diphenylethylenediamine](1,2-dimethylbenzene) ruthenium,

[(S,S)-N-(p-toluenesulfonyl)-1,2-diphenylethylenediamine] (1,3-dimethylbenzene) ruthenium,

[(R,R)-N-(p-toluenesulfonyl)-1,2-diphenylethylenediamine](1,3-dimethylbenzene) ruthenium,

[(S,S)-N-(p-toluenesulfonyl)-1,2-diphenylethylenediamine] (1,4-dimethylbenzene) ruthenium,

[(R,R)-N-(p-toluenesulfonyl)-1,2-diphenylethylenediamine](1,4-dimethylbenzene) ruthenium,

[(S,S)-N-(p-toluenesulfonyl)-1,2-diphenylethylenediamine](p-cymene) ruthenium,

[(R,R)-N-(p-toluenesulfonyl)-1,2-diphenylethylenediamine](p-cymene) ruthenium,

[(S,S)-N-(p-toluenesulfonyl)-1,2-diphenylethylenediamine](mesitylene) ruthenium,

[(R,R)-N-(p-toluenesulfonyl)-1,2-diphenylethylenediamine](mesitylene) ruthenium,

[(S,S)-N-(p-toluenesulfonyl)-1,2-diphenylethylenediamine](1,2,3-trimethylbenzene) ruthenium,

[(R,R)-N-(p-toluenesulfonyl)-1,2-diphenylethylenediamine](1,2,3-trimethylbenzene) ruthenium,

[(S,S)-N-(p-toluenesulfonyl)-1,2-diphenylethylenediamine](1,2,4-trimethylbenzene) ruthenium,

[(R,R)-N-(p-toluenesulfonyl)-1,2-diphenylethylenediamine](1,2,4-trimethylbenzene) ruthenium,

[(S,S)-N-(p-toluenesulfonyl)-1,2-diphenylethylenediamine](1,2,4,5-tetramethylbenzene) ruthenium,

[(R,R)-N-(p-toluenesulfonyl)-1,2-diphenylethylenediamine](1,2,4,5-tetramethylbenzene) ruthenium,

[(S,S)-N-(p-toluenesulfonyl)-1,2-diphenylethylenediamine](1,2,3,4-tetramethylbenzene) ruthenium,

[(R,R)-N-(p-toluenesulfonyl)-1,2-diphenylethylenediamine](1,2,3,4-tetramethylbenzene) ruthenium,

[(S,S)-N-(p-toluenesulfonyl)-1,2-diphenylethylenediamine](1,2,3,5-tetramethylbenzene) ruthenium,

[(R,R)-N-(p-toluenesulfonyl)-1,2-diphenylethylenediamine](1,2,3,5-tetramethylbenzene) ruthenium,

[(S,S)-N-(p-toluenesulfonyl)-1,2-diphenylethylenediamine](1,2,3,4,5-pentamethylmethylbenzene) ruthenium,

[(R,R)-N-(p-toluenesulfonyl)-1,2-diphenylethylenediamine](1,2,3,4,5-pentamethylbenzene) ruthenium,

[(S,S)-N-(p-toluenesulfonyl)-1,2-diphenylethylenediamine](hexamethylbenzene) ruthenium,

[(R,R)-N-(p-toluenesulfonyl)-1,2-diphenylethylenediamine](hexamethylbenzene) ruthenium,

[(S,S)-N-methanesulfonyl-1,2-diphenylethylenediamine]benzene ruthenium,

[(R,R)-N-methanesulfonyl-1,2-diphenylethylenediamine]benzene ruthenium,

[(S,S)-N-methanesulfonyl-1,2-diphenylethylenediamine](methylbenzene) ruthenium,

[(R,R)-N-methanesulfonyl-1,2-diphenylethylenediamine](methylbenzene) ruthenium,

[(S,S)-N-methanesulfonyl-1,2-diphenylethylenediamine](1,2-dimethylbenzene) ruthenium,

[(R,R)-N-methanesulfonyl-1,2-diphenylethylenediamine](1,2-dimethylbenzene) ruthenium,

[(S,S)-N-methanesulfonyl-1,2-diphenylethylenediamine](1,3-dimethylbenzene) ruthenium,

[(R,R)-N-methanesulfonyl-1,2-diphenylethylenediamine](1,3-dimethylbenzene) ruthenium,

[(S,S)-N-methanesulfonyl-1,2-diphenylethylenediamine](1,4-dimethylbenzene) ruthenium,

[(R,R)-N-methanesulfonyl-1,2-diphenylethylenediamine](1,4-dimethylbenzene) ruthenium,

[(S,S)-N-methanesulfonyl-1,2-diphenylethylenediamine](p-cymene) ruthenium,

[(R,R)-N-methanesulfonyl-1,2-diphenylethylenediamine](p-cymene) ruthenium,

[(S,S)-N-methanesulfonyl-1,2-diphenylethylenediamine](mesitylene) ruthenium,

[(R,R)-N-methanesulfonyl-1,2-diphenylethylenediamine](mesitylene) ruthenium,

[(S,S)-N-methanesulfonyl-1,2-diphenylethylenediamine](1,2,3-trimethylbenzene) ruthenium,

[(R,R)-N-methanesulfonyl-1,2-diphenylethylenediamine](1,2,3-trimethylbenzene) ruthenium,

[(S,S)-N-methanesulfonyl-1,2-diphenylethylenediamine](1,2,4-trimethylbenzene) ruthenium,

[(R,R)-N-methanesulfonyl-1,2-diphenylethylenediamine](1,2,4-trimethylbenzene) ruthenium,

[(S,S)-N-methanesulfonyl-1,2-diphenylethylenediamine](1,2,4,5-tetramethylbenzene) ruthenium,

[(R,R)-N-methanesulfonyl-1,2-diphenylethylenediamine](1,2,4,5-tetramethylbenzene) ruthenium,

[(S,S)-N-methanesulfonyl-1,2-diphenylethylenediamine](1,2,3,5-tetramethylbenzene) ruthenium,

[(R,R)-N-methanesulfonyl-1,2-diphenylethylenediamine](1,2,3,5-tetramethylbenzene) ruthenium,

[(S,S)-N-methanesulfonyl-1,2-diphenylethylenediamine](1,2,3,4-tetramethylbenzene) ruthenium,

[(R,R)-N-methanesulfonyl-1,2-diphenylethylenediamine](1,2,3,4-tetramethylbenzene) ruthenium,

[(S,S)-N-methanesulfonyl-1,2-diphenylethylenediamine](1,2,3,4,5-pentamethylbenzene) ruthenium,

[(R,R)-N-methanesulfonyl-1,2-diphenylethylenediamine](1,2,3,4,5-pentamethylbenzene) ruthenium,

[(S,S)-N-methanesulfonyl-1,2-diphenylethylenediamine](hexamethylbenzene) ruthenium,

[(R,R)-N-methanesulfonyl-1,2-diphenylethylenediamine](hexamethylbenzene) ruthenium,

[(S,S)-N-trifluoromethanesulfonyl-1,2-diphenylethylenediamine]benzene ruthenium,

[(R,R)-N-trifluoromethanesulfonyl-1,2-diphenylethylenediamine]benzene ruthenium,

[(S,S)-N-trifluoromethanesulfonyl-1,2-diphenylethylenediamine](methylbenzene) ruthenium,

[(R,R)-N-trifluoromethanesulfonyl-1,2-diphenylethylenediamine](methylbenzene) ruthenium,

[(S,S)-N-trifluoromethanesulfonyl-1,2-diphenylethylenediamine](1,2-dimethylbenzene) ruthenium,

[(R,R)-N-trifluoromethanesulfonyl-1,2-diphenylethylenediamine](1,2-dimethylbenzene) ruthenium,

[(S,S)-N-trifluoromethanesulfonyl-1,2-diphenylethylenediamine](1,3-dimethylbenzene) ruthenium,

[(R,R)-N-trifluoromethanesulfonyl-1,2-diphenylethylenediamine](1,3-dimethylbenzene) ruthenium,

[(S,S)-N-trifluoromethanesulfonyl-1,2-diphenylethylenediamine](1,4-dimethylbenzene) ruthenium,

[(R,R)-N-trifluoromethanesulfonyl-1,2-diphenylethylenediamine](1,4-dimethylbenzene) ruthenium,

[(S,S)-N-trifluoromethanesulfonyl-1,2-diphenylethylenediamine](p-cymene) ruthenium,

[(R,R)-N-trifluoromethanesulfonyl-1,2-diphenylethylenediamine](p-cymene) ruthenium,

[(S,S)-N-trifluoromethanesulfonyl-1,2-diphenylethylenediamine](mesitylene) ruthenium,

[(R,R)-N-trifluoromethanesulfonyl-1,2-diphenylethylenediamine](mesitylene) ruthenium,

[(S,S)-N-trifluoromethanesulfonyl-1,2-diphenylethylenediamine](1,2,3-trimethylbenzene) ruthenium,

[(R,R)-N-trifluoromethanesulfonyl-1,2-diphenylethylenediamine](1,2,3-trimethylbenzene) ruthenium,

[(S,S)-N-trifluoromethanesulfonyl-1,2-diphenylethylenediamine](1,2,4-trimethylbenzene) ruthenium,

[(R,R)-N-trifluoromethanesulfonyl-1,2-diphenylethylenediamine](1,2,4-trimethylbenzene) ruthenium,

[(S,S)-N-trifluoromethanesulfonyl-1,2-diphenylethylenediamine](1,2,4,5-tetramethylbenzene) ruthenium,

[(R,R)-N-trifluoromethanesulfonyl-1,2-diphenylethylenediamine](1,2,4,5-tetramethylbenzene) ruthenium,

[(S,S)-N-trifluoromethanesulfonyl-1,2-diphenylethylenediamine](1,2,3,5-tetramethylbenzene) ruthenium,

[(R,R)-N-trifluoromethanesulfonyl-1,2-diphenylethylenediamine](1,2,3,5-tetramethylbenzene) ruthenium,

[(S,S)-N-trifluoromethanesulfonyl-1,2-diphenylethylenediamine](1,2,3,4-tetramethylbenzene) ruthenium,

[(R,R)-N-trifluoromethanesulfonyl-1,2-diphenylethylenediamine](1,2,3,4-tetramethylbenzene) ruthenium,

[(S,S)-N-trifluoromethanesulfonyl-1,2-diphenylethylenediamine](1,2,3,4,5-pentamethylbenzene) ruthenium,

[(R,R)-N-trifluoromethanesulfonyl-1,2-diphenylethylenediamine](1,2,3,4,5-pentamethylbenzene) ruthenium,

[(S,S)-N-trifluoromethanesulfonyl-1,2-diphenylethylenediamine](hexamethylbenzene) ruthenium,

[(R,R)-N-trifluoromethanesulfonyl-1,2-diphenylethylenediamine](hexamethylbenzene) ruthenium,

[(S,S)-N-(p-toluenesulfonyl)-1,2-cyclohexanediamine]benzene ruthenium, [(R,R)-N-(p-toluenesulfonyl)-1,2-cyclohexanediamine]benzene ruthenium,

[(S,S)-N-(p-toluenesulfonyl)-1,2-cyclohexanediamine](methylbenzene) ruthenium,

[(R,R)-N-(p-toluenesulfonyl)-1,2-cyclohexanediamine](methylbenzene) ruthenium,

[(S,S)-N-(p-toluenesulfonyl)-1,2-cyclohexanediamine](1,2-dimethylbenzene) ruthenium,

[(R,R)-N-(p-toluenesulfonyl)-1,2-cyclohexanediamine](1,2-dimethylbenzene) ruthenium,

[(S,S)-N-(p-toluenesulfonyl)-1,2-cyclohexanediamine](1,3-dimethylbenzene) ruthenium,

[(R,R)-N-(p-toluenesulfonyl)-1,2-cyclohexanediamine](1,3-dimethylbenzene) ruthenium,

[(S,S)-N-(p-toluenesulfonyl)-1,2-cyclohexanediamine](1,4-dimethylbenzene) ruthenium,

[(R,R)-N-(p-toluenesulfonyl)-1,2-cyclohexanediamine](1,4-dimethylbenzene) ruthenium,

[(S,S)-N-(p-toluenesulfonyl)-1,2-cyclohexanediamine](p-cymene) ruthenium, [(R,R)-N-(p-toluenesulfonyl)-1,2-cyclohexanediamine](p-cymene) ruthenium,

[(S,S)-N-(p-toluenesulfonyl)-1,2-cyclohexanediamine](mesitylene) ruthenium,

[(R,R)-N-(p-toluenesulfonyl)-1,2-cyclohexanediamine](mesitylene) ruthenium,

[(S,S)-N-(p-toluenesulfonyl)-1,2-cyclohexanediamine](1,2,3-trimethylbenzene) ruthenium,

[(R,R)-N-(p-toluenesulfonyl)-1,2-cyclohexanediamine](1,2,3-trimethylbenzene) ruthenium,

[(S,S)-N-(p-toluenesulfonyl)-1,2-cyclohexanediamine](1,2,4-trimethylbenzene) ruthenium,

[(R,R)-N-(p-toluenesulfonyl)-1,2-cyclohexanediamine](1,2,4-trimethylbenzene) ruthenium,

[(S,S)-N-(p-toluenesulfonyl)-1,2-cyclohexanediamine](1,2,4,5-tetramethylbenzene) ruthenium,

[(R,R)-N-(p-toluenesulfonyl)-1,2-cyclohexanediamine](1,2,4,5-tetramethylbenzene) ruthenium,

[(S,S)-N-(p-toluenesulfonyl)-1,2-cyclohexanediamine](1,2,3,4-tetramethylbenzene) ruthenium,

[(R,R)-N-(p-toluenesulfonyl)-1,2-cyclohexanediamine](1,2,3,4-tetramethylbenzene) ruthenium,

[(S,S)-N-(p-toluenesulfonyl)-1,2-cyclohexanediamine](1,2,3,5-tetramethylbenzene) ruthenium,

[(R,R)-N-(p-toluenesulfonyl)-1,2-cyclohexanediamine](1,2,3,5-tetramethylbenzene) ruthenium,

[(S,S)-N-(p-toluenesulfonyl)-1,2-cyclohexanediamine](1,2,3,4,5-pentamethylbenzene) ruthenium,

[(R,R)-N-(p-toluenesulfonyl)-1,2-cyclohexanediamine](1,2,3,4,5-pentamethylbenzene) ruthenium,

[(S,S)-N-(p-toluenesulfonyl)-1,2-cyclohexanediamine](hexamethylbenzene) ruthenium,

[(R,R)-N-(p-toluenesulfonyl)-1,2-cyclohexanediamine](hexamethylbenzene) ruthenium,

[(S,S)-N-methanesulfonyl-1,2-cyclohexanediamine]benzene ruthenium, [(R,R)-N-methanesulfonyl-1,2-cyclohexanediamine]benzene ruthenium,

[(S,S)-N-methanesulfonyl-1,2-cyclohexanediamine](methylbenzene) ruthenium,

[(R,R)-N-methanesulfonyl-1,2-cyclohexanediamine](methylbenzene) ruthenium,

[(S,S)-N-methanesulfonyl-1,2-cyclohexanediamine](1,2-dimethylbenzene) ruthenium,

[(R,R)-N-methanesulfonyl-1,2-cyclohexanediamine](1,2-dimethylbenzene) ruthenium,

[(S,S)-N-methanesulfonyl-1,2-cyclohexanediamine](1,3-dimethylbenzene) ruthenium,

[(R,R)-N-methanesulfonyl-1,2-cyclohexanediamine](1,3-dimethylbenzene) ruthenium,

[(S,S)-N-methanesulfonyl-1,2-cyclohexanediamine](1,4-dimethylbenzene) ruthenium,

[(R,R)-N-methanesulfonyl-1,2-cyclohexanediamine](1,4-dimethylbenzene) ruthenium,

[(S,S)-N-methanesulfonyl-1,2-cyclohexanediamine](p-cymene) ruthenium, [(R,R)-N-methanesulfonyl-1,2-cyclohexanediamine](p-cymene) ruthenium,

[(S,S)-N-methanesulfonyl-1,2-cyclohexanediamine](mesitylene) ruthenium, [(R,R)-N-methanesulfonyl-1,2-cyclohexanediamine](mesitylene) ruthenium,

[(S,S)-N-methanesulfonyl-1,2-cyclohexanediamine](1,2,3-trimethylbenzene) ruthenium,

[(R,R)-N-methanesulfonyl-1,2-cyclohexanediamine](1,2,3-trimethylbenzene) ruthenium,

[(S,S)-N-methanesulfonyl-1,2-cyclohexanediamine](1,2,4-trimethylbenzene) ruthenium,

[(R,R)-N-methanesulfonyl-1,2-cyclohexanediamine](1,2,4-trimethylbenzene) ruthenium,

[(S,S)-N-methanesulfonyl-1,2-cyclohexanediamine](1,2,4,5-tetramethylbenzene) ruthenium,

[(R,R)-N-methanesulfonyl-1,2-cyclohexanediamine](1,2,4,5-tetramethylbenzene) ruthenium,

[(S,S)-N-methanesulfonyl-1,2-cyclohexanediamine](1,2,3,5-tetramethylbenzene) ruthenium,

[(R,R)-N-methanesulfonyl-1,2-cyclohexanediamine](1,2,3,5-tetramethylbenzene) ruthenium,

[(S,S)-N-methanesulfonyl-1,2-cyclohexanediamine](1,2,3,4-tetramethylbenzene) ruthenium,

[(R,R)-N-methanesulfonyl-1,2-cyclohexanediamine](1,2,3,4-tetramethylbenzene) ruthenium,

[(S,S)-N-methanesulfonyl-1,2-cyclohexanediamine](1,2,3,4,5-pentamethylbenzene) ruthenium,

[(R,R)-N-methanesulfonyl-1,2-cyclohexanediamine](1,2,3,4,5-pentamethylbenzene) ruthenium,

[(S,S)-N-methanesulfonyl-1,2-cyclohexanediamine](hexamethylbenzene) ruthenium,

[(R,R)-N-methanesulfonyl-1,2-cyclohexanediamine](hexamethylbenzene) ruthenium,

[(S,S)-N-trifluoromethanesulfonyl-1,2-cyclohexanediamine]benzene ruthenium,

[(R,R)-N-trifluoromethanesulfonyl-1,2-cyclohexanediamine]benzene ruthenium,

[(S,S)-N-trifluoromethanesulfonyl-1,2-cyclohexanediamine](methylbenzene) ruthenium,

[(R,R)-N-trifluoromethanesulfonyl-1,2-cyclohexanediamine](methylbenzene) ruthenium,

[(S,S)-N-trifluoromethanesulfonyl)-1,2-cyclohexanediamine](1,2-dimethylbenzene) ruthenium,

[(R,R)-N-trifluoromethanesulfonyl-1,2-cyclohexanediamine](1,2-dimethylbenzene) ruthenium,

[(S,S)-N-trifluoromethanesulfonyl-1,2-cyclohexanediamine](1,3-dimethylbenzene) ruthenium,

[(R,R)-N-trifluoromethanesulfonyl-1,2-cyclohexanediamine](1,3-dimethylbenzene) ruthenium,

[(S,S)-N-trifluoromethanesulfonyl-1,2-cyclohexanediamine](1,4-dimethylbenzene) ruthenium,

[(R,R)-N-trifluoromethanesulfonyl-1,2-cyclohexanediamine](1,4-dimethylbenzene) ruthenium,

[(S,S)-N-trifluoromethanesulfonyl-1,2-cyclohexanediamine](p-cymene) ruthenium,

[(R,R)-N-trifluoromethanesulfonyl-1,2-cyclohexanediamine](p-cymene) ruthenium,

[(S,S)-N-trifluoromethanesulfonyl-1,2-cyclohexanediamine](mesitylene) ruthenium,

[(R,R)-N-trifluoromethanesulfonyl-1,2-cyclohexanediamine](mesitylene) ruthenium,

[(S,S)-N-trifluoromethanesulfonyl-1,2-cyclohexanediamine](1,2,3-trimethylbenzene) ruthenium,

[(R,R)-N-trifluoromethanesulfonyl-1,2-cyclohexanediamine](1,2,3-trimethylbenzene) ruthenium,

[(S,S)-N-trifluoromethanesulfonyl-1,2-cyclohexanediamine](1,2,4-trimethylbenzene) ruthenium,

[(R,R)-N-trifluoromethanesulfonyl-1,2-cyclohexanediamine](1,2,4-trimethylbenzene) ruthenium,

[(S,S)-N-trifluoromethanesulfonyl-1,2-cyclohexanediamine](1,2,4,5-tetramethylbenzene) ruthenium,

[(R,R)-N-trifluoromethanesulfonyl-1,2-cyclohexanediamine](1,2,4,5-tetramethylbenzene) ruthenium,

[(S,S)-N-trifluoromethanesulfonyl-1,2-cyclohexanediamine](1,2,3,5-tetramethylbenzene) ruthenium,

[(R,R)-N-trifluoromethanesulfonyl-1,2-cyclohexanediamine](1,2,3,5-tetramethylbenzene) ruthenium,

[(S,S)-N-trifluoromethanesulfonyl-1,2-cyclohexanediamine](1,2,3,4-tetramethylbenzene) ruthenium,

[(R,R)-N-trifluoromethanesulfonyl-1,2-cyclohexanediamine](1,2,3,4-tetramethylbenzene) ruthenium,

[(S,S)-N-trifluoromethanesulfonyl-1,2-cyclohexanediamine](1,2,3,4,5-pentamethylbenzene) ruthenium,

[(R,R)-N-trifluoromethanesulfonyl-1,2-cyclohexanediamine](1,2,3,4,5-pentamethylbenzene) ruthenium,

[(S,S)-N-trifluoromethanesulfonyl-1,2-cyclohexanediamine](hexamethylbenzene) ruthenium, and

[(R,R)-N-trifluoromethanesulfonyl-1,2-cyclohexanediamine](hexamethylbenzene) ruthenium.

Examples of the ruthenium hydrido complex include hydrido

[(S,S)-N-(p-toluenesulfonyl)-1,2-diphenylethylenediamine]benzene ruthenium, hydrido

[(R,R)-N-(p-toluenesulfonyl)-1,2-diphenylethylenediamine]benzene ruthenium, hydrido

[(S,S)-N-(p-toluenesulfonyl)-1,2-diphenylethylenediamine](methylbenzene) ruthenium, hydrido

[(R,R)-N-(p-toluenesulfonyl)-1,2-diphenylethylenediamine](methylbenzene) ruthenium, hydrido

[(S,S)-N-(p-toluenesulfonyl)-1,2-diphenylethylenediamine](1,2-dimethylbenzene) ruthenium, hydrido

[(R,R)-N-(p-toluenesulfonyl)-1,2-diphenylethylenediamine](1,2-dimethylbenzene) ruthenium, hydrido

[(S,S)-N-(p-toluenesulfonyl)-1,2-diphenylethylenediamine](1,3-dimethylbenzene) ruthenium, hydrido

[(R,R)-N-(p-toluenesulfonyl)-1,2-diphenylethylenediamine](1,3-dimethylbenzene) ruthenium, hydrido

[(S,S)-N-(p-toluenesulfonyl)-1,2-diphenylethylenediamine](1,4-dimethylbenzene) ruthenium, hydrido

[(R,R)-N-(p-toluenesulfonyl)-1,2-diphenylethylenediamine](1,4-dimethylbenzene) ruthenium, hydrido

[(S,S)-N-(p-toluenesulfonyl)-1,2-diphenylethylenediamine](p-cymene) ruthenium, hydrido

[(R,R)-N-(p-toluenesulfonyl)-1,2-diphenylethylenediamine](p-cymene) ruthenium, hydrido

[(S,S)-N-(p-toluenesulfonyl)-1,2-diphenylethylenediamine](mesitylene) ruthenium, hydrido

[(R,R)-N-(p-toluenesulfonyl)-1,2-diphenylethylenediamine](mesitylene) ruthenium, hydrido

[(S,S)-N-(p-toluenesulfonyl)-1,2-diphenylethylenediamine](1,2,3-trimethylbenzene) ruthenium, hydrido

[(R,R)-N-(p-toluenesulfonyl)-1,2-diphenylethylenediamine](1,2,3-trimethylbenzene) ruthenium, hydrido

[(S,S)-N-(p-toluenesulfonyl)-1,2-diphenylethylenediamine](1,2,4-trimethylbenzene) ruthenium, hydrido

[(R,R)-N-(p-toluenesulfonyl)-1,2-diphenylethylenediamine](1,2,4-trimethylbenzene) ruthenium, hydrido

[(S,S)-N-(p-toluenesulfonyl)-1,2-diphenylethylenediamine](1,2,4,5-tetramethylbenzene) ruthenium, hydrido

[(R,R)-N-(p-toluenesulfonyl)-1,2-diphenylethylenediamine](1,2,4,5-tetramethylbenzene) ruthenium, hydrido

[(S,S)-N-(p-toluenesulfonyl)-1,2-diphenylethylenediamine](1,2,3,5-tetramethylbenzene) ruthenium, hydrido

[(R,R)-N-(p-toluenesulfonyl)-1,2-diphenylethylenediamine](1,2,3,5-tetramethylbenzene) ruthenium, hydrido

[(S,S)-N-(p-toluenesulfonyl)-1,2-diphenylethylenediamine](1,2,3,4-tetramethylbenzene) ruthenium, hydrido

[(R,R)-N-(p-toluenesulfonyl)-1,2-diphenylethylenediamine](1,2,3,4-tetramethylbenzene) ruthenium, hydrido

[(S,S)-N-(p-toluenesulfonyl)-1,2-diphenylethylenediamine](1,2,3,4,5-pentamethylbenzene) ruthenium, hydrido

[(R,R)-N-(p-toluenesulfonyl)-1,2-diphenylethylenediamine](1,2,3,4,5-pentamethylbenzene) ruthenium, hydrido

[(S,S)-N-(p-toluenesulfonyl)-1,2-diphenylethylenediamine](hexamethylbenzene) ruthenium, hydrido

[(R,R)-N-(p-toluenesulfonyl)-1,2-diphenylethylenediamine](hexamethylbenzene) ruthenium, hydrido

[(S,S)-N-methanesulfonyl-1,2-diphenylethylenediamine]benzene ruthenium, hydrido

[(R,R)-N-methanesulfonyl-1,2-diphenylethylenediamine]benzene ruthenium, hydrido

[(S,S)-N-methanesulfonyl-1,2-diphenylethylenediamine](methylbenzene) ruthenium, hydrido

[(R,R)-N-methanesulfonyl-1,2-diphenylethylenediamine](methylbenzene) ruthenium, hydrido

[(S,S)-N-methanesulfonyl-1,2-diphenylethylenediamine](1,2-dimethylbenzene) ruthenium, hydrido

[(R,R)-N-methanesulfonyl-1,2-diphenylethylenediamine](1,2-dimethylbenzene) ruthenium, hydrido

[(S,S)-N-methanesulfonyl-1,2-diphenylethylenediamine](1,3-dimethylbenzene) ruthenium, hydrido

[(R,R)-N-methanesulfonyl-1,2-diphenylethylenediamine](1,3-dimethylbenzene) ruthenium, hydrido

[(S,S)-N-methanesulfonyl-1,2-diphenylethylenediamine](1,4-dimethylbenzene) ruthenium, hydrido

[(R,R)-N-methanesulfonyl-1,2-diphenylethylenediamine](1,4-dimethylbenzene) ruthenium, hydrido

[(S,S)-N-methanesulfonyl-1,2-diphenylethylenediamine](p-cymene) ruthenium, hydrido

[(R,R)-N-methanesulfonyl-1,2-diphenylethylenediamine](p-cymene) ruthenium, hydrido

[(S,S)-N-methanesulfonyl-1,2-diphenylethylenediamine](mesitylene) ruthenium, hydrido

[(R,R)-N-methanesulfonyl-1,2-diphenylethylenediamine](mesitylene) ruthenium, hydrido

[(S,S)-N-methanesulfonyl-1,2-diphenylethylenediamine](1,2,3-trimethylbenzene) ruthenium, hydrido

[(R,R)-N-methanesulfonyl-1,2-diphenylethylenediamine](1,2,3-trimethylbenzene) ruthenium, hydrido

[(S,S)-N-methanesulfonyl-1,2-diphenylethylenediamine](1,2,4-trimethylbenzene) ruthenium, hydrido

[(R,R)-N-methanesulfonyl-1,2-diphenylethylenediamine](1,2,4-trimethylbenzene) ruthenium, hydrido

[(S,S)-N-methanesulfonyl-1,2-diphenylethylenediamine](1,2,4,5-tetramethylbenzene) ruthenium, hydrido

[(R,R)-N-methanesulfonyl-1,2-diphenylethylenediamine](1,2,4,5-tetramethylbenzene) ruthenium, hydrido

[(S,S)-N-methanesulfonyl-1,2-diphenylethylenediamine](1,2,3,5-tetramethylbenzene) ruthenium, hydrido

[(R,R)-N-methanesulfonyl-1,2-diphenylethylenediamine](1,2,3,5-tetramethylbenzene) ruthenium, hydrido

[(S,S)-N-methanesulfonyl-1,2-diphenylethylenediamine](1,2,3,4-tetramethylbenzene) ruthenium, hydrido

[(R,R)-N-methanesulfonyl-1,2-diphenylethylenediamine](1,2,3,4-tetramethylbenzene) ruthenium, hydrido

[(S,S)-N-methanesulfonyl-1,2-diphenylethylenediamine](1,2,3,4,5-pentamethylbenzene) ruthenium, hydrido

[(R,R)-N-methanesulfonyl-1,2-diphenylethylenediamine](1,2,3,4,5-pentamethylbenzene) ruthenium, hydrido

[(S,S)-N-methanesulfonyl-1,2-diphenylethylenediamine](hexamethylbenzene) ruthenium, hydrido

[(R,R)-N-methanesulfonyl-1,2-diphenylethylenediamine](hexamethylbenzene )ruthenium, hydrido

[(S,S)-N-trifluoromethanesulfonyl-1,2-diphenylethylenediamine]benzene ruthenium, hydrido

[(R,R)-N-trifluoromethanesulfonyl-1,2-diphenylethylenediamine]benzene ruthenium, hydrido

[(S,S)-N-trifluoromethanesulfonyl-1,2-diphenylethylenediamine](methylbenzene) ruthenium, hydrido

[(R,R)-N-trifluoromethanesulfonyl-1,2-diphenylethylenediamine](methylbenzene) ruthenium, hydrido

[(S,S)-N-trifluoromethanesulfonyl-1,2-diphenylethylenediamine](1,2-dimethylbenzene) ruthenium, hydrido

[(R,R)-N-trifluoromethanesulfonyl-1,2-diphenylethylenediamine](1,2-dimethylbenzene) ruthenium, hydrido

[(S,S)-N-trifluoromethanesulfonyl-1,2-diphenylethylenediamine](1,3-dimethylbenzene) ruthenium, hydrido

[(R,R)-N-trifluoromethanesulfonyl-1,2-diphenylethylenediamine](1,3-dimethylbenzene) ruthenium, hydrido

[(S,S)-N-trifluoromethanesulfonyl-1,2-diphenylethylenediamine](1,4-dimethylbenzene) ruthenium, hydrido

[(R,R)-N-trifluoromethanesulfonyl-1,2-diphenylethylenediamine](1,4-dimethylbenzene) ruthenium, hydrido

[(S,S)-N-trifluoromethanesulfonyl-1,2-diphenylethylenediamine](p-cymene) ruthenium, hydrido

[(R,R)-N-trifluoromethanesulfonyl-1,2-diphenylethylenediamine](p-cymene) ruthenium, hydrido

[(S,S)-N-trifluoromethanesulfonyl-1,2-diphenylethylenediamine](mesitylene) ruthenium, hydrido

[(R,R)-N-trifluoromethanesulfonyl-1,2-diphenylethylenediamine](mesitylene) ruthenium, hydrido

[(S,S)-N-trifluoromethanesulfonyl-1,2-diphenylethylenediamine](1,2,3-trimethylbenzene) ruthenium, hydrido

[(R,R)-N-trifluoromethanesulfonyl-1,2-diphenylethylenediamine](1,2,3-trimethylbenzene) ruthenium, hydrido

[(S,S)-N-trifluoromethanesulfonyl-1,2-diphenylethylenediamine](1,2,4-trimethylbenzene) ruthenium, hydrido

[(R,R)-N-trifluoromethanesulfonyl-1,2-diphenylethylenediamine](1,2,4-trimethylbenzene) ruthenium, hydrido

[(S,S)-N-trifluoromethanesulfonyl-1,2-diphenylethylenediamine](1,2,4,5-tetramethylbenzene) ruthenium, hydrido

[(R,R)-N-trifluoromethanesulfonyl-1,2-diphenylethylenediamine](1,2,4,5-tetramethylbenzene) ruthenium, hydrido

[(S,S)-N-trifluoromethanesulfonyl-1,2-diphenylethylenediamine](1,2,3,5-tetramethylbenzene) ruthenium, hydrido

[(R,R)-N-trifluoromethanesulfonyl-1,2-diphenylethylenediamine](1,2,3,5-tetramethylbenzene) ruthenium, hydrido

[(S,S)-N-trifluoromethanesulfonyl-1,2-diphenylethylenediamine](1,2,3,4-tetramethylbenzene) ruthenium, hydrido

[(R,R)-N-trifluoromethanesulfonyl-1,2-diphenylethylenediamine](1,2,3,4-tetramethylbenzene) ruthenium, hydrido

[(S,S)-N-trifluoromethanesulfonyl-1,2-diphenylethylenediamine](1,2,3,4,5-pentamethylbenzene) ruthenium, hydrido

[(R,R)-N-trifluoromethanesulfonyl-1,2-diphenylethylenediamine](1,2,3,4,5-pentamethylbenzene) ruthenium, hydrido

[(S,S)-N-trifluoromethanesulfonyl-1,2-diphenylethylenediamine](hexamethylbenzene) ruthenium, hydrido

[(R,R)-N-trifluoromethanesulfonyl-1,2-diphenylethylenediamine](hexamethylbenzene) ruthenium, hydrido [(S,S)-N-(p-toluenesulfonyl)-1,2-cyclohexanediamine]benzene ruthenium, hydrido

[(R,R)-N-(p-toluenesulfonyl)-1,2-cyclohexanediamine]benzene ruthenium, hydrido

[(S,S)-N-(p-toluenesulfonyl)-1,2-cyclohexanediamine](methylbenzene) ruthenium, hydrido

[(R,R)-N-(p-toluenesulfonyl)-1,2-cyclohexanediamine](methylbenzene) ruthenium, hydrido

[(S,S)-N-(p-toluenesulfonyl)-1,2-cyclohexanediamine](1,2-dimethylbenzene) ruthenium, hydrido

[(R,R)-N-(p-toluenesulfonyl)-1,2-cyclohexanediamine](1,2-dimethylbenzene) ruthenium, hydrido

[(S,S)-N-(p-toluenesulfonyl)-1,2-cyclohexanediamine](1,3-dimethylbenzene) ruthenium, hydrido

[(R,R)-N-(p-toluenesulfonyl)-1,2-cyclohexanediamine](1,3-dimethylbenzene) ruthenium, hydrido

[(S,S)-N-(p-toluenesulfonyl)-1,2-cyclohexanediamine](1,4-dimethylbenzene) ruthenium, hydrido

[(R,R)-N-(p-toluenesulfonyl)-1,2-cyclohexanediamine](1,4-dimethylbenzene) ruthenium, hydrido

[(S,S)-N-(p-toluenesulfonyl)-1,2-cyclohexanediamine](p-cymene) ruthenium, hydrido

[(R,R)-N-(p-toluenesulfonyl)-1,2-cyclohexanediamine](p-cymene) ruthenium, hydrido

[(S,S)-N-(p-toluenesulfonyl)-1,2-cyclohexanediamine](mesitylene) ruthenium, hydrido

[(R,R)-N-(p-toluenesulfonyl)-1,2-cyclohexanediamine](mesitylene) ruthenium, hydrido

[(S,S)-N-(p-toluenesulfonyl)-1,2-cyclohexanediamine](1,2,3-trimethylbenzene) ruthenium, hydrido

[(R,R)-N-(p-toluenesulfonyl)-1,2-cyclohexanediamine](1,2,3-trimethylbenzene) ruthenium, hydrido

[(S,S)-N-(p-toluenesulfonyl)-1,2-cyclohexanediamine](1,2,4-trimethylbenzene) ruthenium, hydrido

[(R,R)-N-(p-toluenesulfonyl)-1,2-cyclohexanediamine](1,2,4-trimethylbenzene) ruthenium, hydrido

[(S,S)-N-(p-toluenesulfonyl)-1,2-cyclohexanediamine](1,2,4,5-tetramethylbenzene) ruthenium, hydrido

[(R,R)-N-(p-toluenesulfonyl)-1,2-cyclohexanediamine](1,2,4,5-tetramethylbenzene) ruthenium, hydrido

[(S,S)-N-(p-toluenesulfonyl)-1,2-cyclohexanediamine](1,2,3,5-tetramethylbenzene) ruthenium, hydrido

[(R,R)-N-(p-toluenesulfonyl)-1,2-cyclohexanediamine](1,2,3,5-tetramethylbenzene) ruthenium, hydrido

[(S,S)-N-(p-toluenesulfonyl)-1,2-cyclohexanediamine](1,2,3,4-tetramethylbenzene) ruthenium, hydrido

[(R,R)-N-(p-toluenesulfonyl)-1,2-cyclohexanediamine](1,2,3,4-tetramethylbenzene) ruthenium, hydrido

[(S,S)-N-(p-toluenesulfonyl)-1,2-cyclohexanediamine](1,2,3,4,5-pentamethylbenzene) ruthenium, hydrido

[(R,R)-N-(p-toluenesulfonyl)-1,2-cyclohexanediamine](1,2,3,4,5-pentamethylbenzene) ruthenium, hydrido

[(S,S)-N-(p-toluenesulfonyl)-1,2-cyclohexanediamine](hexamethylbenzene) ruthenium, hydrido

[(R,R)-N-(p-toluenesulfonyl)-1,2-cyclohexanediamine](hexamethylbenzene) ruthenium, hydrido    [(S,S)-N-methanesulfonyl-1,2-cyclohexanediamine]benzene ruthenium, hydrido

[(R,R)-N-methanesulfonyl-1,2-cyclohexanediamine]benzene ruthenium, hydrido

[(S,S)-N-methanesulfonyl-1,2-cyclohexanediamine](methylbenzene) ruthenium, hydrido

[(R,R)-N-methanesulfonyl-1,2-cyclohexanediamine](methylbenzene) ruthenium, hydrido

[(S,S)-N-methanesulfonyl-1,2-cyclohexanediamine](1,2-dimethylbenzene) ruthenium, hydrido

[(R,R)-N-methanesulfonyl-1,2-cyclohexanediamine](1,2-dimethylbenzene) ruthenium, hydrido

[(S,S)-N-methanesulfonyl-1,2-cyclohexanediamine](1,3-dimethylbenzene) ruthenium, hydrido

[(R,R)-N-methanesulfonyl-1,2-cyclohexanediamine](1,3-dimethylbenzene) ruthenium, hydrido

[(S,S)-N-methanesulfonyl-1,2-cyclohexanediamine](1,4-dimethylbenzene) ruthenium, hydrido

[(R,R)-N-methanesulfonyl-1,2-cyclohexanediamine](1,4-dimethylbenzene) ruthenium, hydrido

[(S,S)-N-methanesulfonyl-1,2-cyclohexanediamine](p-cymene) ruthenium, hydrido

[(R,R)-N-methanesulfonyl-1,2-cyclohexanediamine](p-cymene) ruthenium, hydrido

[(S,S)-N-methanesulfonyl-1,2-cyclohexanediamine](mesitylene) ruthenium, hydrido

[(R,R)-N-methanesulfonyl-1,2-cyclohexanediamine](mesitylene) ruthenium, hydrido

[(S,S)-N-methanesulfonyl-1,2-cyclohexanediamine](1,2,3-trimethylbenzene) ruthenium, hydrido

[(R,R)-N-methanesulfonyl-1,2-cyclohexanediamine](1,2,3-trimethylbenzene) ruthenium, hydrido

[(S,S)-N-methanesulfonyl-1,2-cyclohexanediamine](1,2,4-trimethylbenzene) ruthenium, hydrido

[(R,R)-N-methanesulfonyl-1,2-cyclohexanediamine](1,2,4-trimethylbenzene) ruthenium, hydrido

[(S,S)-N-methanesulfonyl-1,2-cyclohexanediamine](1,2,4,5-tetramethylbenzene) ruthenium, hydrido

[(R,R)-N-methanesulfonyl-1,2-cyclohexanediamine](1,2,4,5-tetramethylbenzene) ruthenium, hydrido

[(S,S)-N-methanesulfonyl-1,2-cyclohexanediamine](1,2,3,5-tetramethylbenzene) ruthenium, hydrido

[(R,R)-N-methanesulfonyl-1,2-cyclohexanediamine](1,2,3,5-tetramethylbenzene) ruthenium, hydrido

[(S,S)-N-methanesulfonyl-1,2-cyclohexanediamine](1,2,3,4-tetramethylbenzene) ruthenium, hydrido

[(R,R)-N-methanesulfonyl-1,2-cyclohexanediamine](1,2,3,4-tetramethylbenzene) ruthenium, hydrido

[(S,S)-N-methanesulfonyl-1,2-cyclohexanediamine](1,2,3,4,5-pentamethylbenzene) ruthenium, hydrido

[(R,R)-N-methanesulfonyl-1,2-cyclohexanediamine](1,2,3,4,5-pentamethylbenzene) ruthenium, hydrido

[(S,S)-N-methanesulfonyl-1,2-cyclohexanediamine](hexamethylbenzene) ruthenium, hydrido

[(R,R)-N-methanesulfonyl-1,2-cyclohexanediamine](hexamethylbenzene) ruthenium, hydrido

[(S,S)-N-trifluoromethanesulfonyl-1,2-cyclohexanediamine]benzene ruthenium, hydrido

[(R,R)-N-trifluoromethanesulfonyl-1,2-cyclohexanediamine]benzene ruthenium, hydrido

[(S,S)-N-trifluoromethanesulfonyl-1,2-cyclohexanediamine](methylbenzene) ruthenium, hydrido

[(R,R)-N-trifluoromethanesulfonyl-1,2-cyclohexanediamine](methylbenzene) ruthenium, hydrido

[(S,S)-N-trifluoromethanesulfonyl-1,2-cyclohexanediamine](1,2-dimethylbenzene) ruthenium, hydrido

[(R,R)-N-trifluoromethanesulfonyl-1,2-cyclohexanediamine](1,2-dimethylbenzene) ruthenium, hydrido

[(S,S)-N-trifluoromethanesulfonyl-1,2-cyclohexanediamine](1,3-dimethylbenzene) ruthenium, hydrido

[(R,R)-N-trifluoromethanesulfonyl-1,2-cyclohexanediamine](1,3-dimethylbenzene) ruthenium, hydrido

[(S,S)-N-trifluoromethanesulfonyl-1,2-cyclohexanediamine](1,4-dimethylbenzene) ruthenium, hydrido

[(R,R)-N-trifluoromethanesulfonyl-1,2-cyclohexanediamine](1,4-dimethylbenzene) ruthenium, hydrido

[(S,S)-N-trifluoromethanesulfonyl-1,2-cyclohexanediamine](p-cymene) ruthenium, hydrido

[(R,R)-N-trifluoromethanesulfonyl-1,2-cyclohexanediamine](p-cymene) ruthenium, hydrido

[(S,S)-N-trifluoromethanesulfonyl-1,2-cyclohexanediamine](mesitylene) ruthenium, hydrido

[(R,R)-N-trifluoromethanesulfonyl-1,2-cyclohexanediamine](mesitylene) ruthenium, hydrido

[(S,S)-N-trifluoromethanesulfonyl-1,2-cyclohexanediamine](1,2,3-trimethylbenzene) ruthenium, hydrido

[(R,R)-N-trifluoromethanesulfonyl-1,2-cyclohexanediamine](1,2,3-trimethylbenzene) ruthenium, hydrido

[(S,S)-N-trifluoromethanesulfonyl-1,2-cyclohexanediamine](1,2,4-trimethylbenzene) ruthenium, hydrido

[(R,R)-N-trifluoromethanesulfonyl-1,2-cyclohexanediamine](1,2,4-trimethylbenzene) ruthenium, hydrido

[(S,S)-N-trifluoromethanesulfonyl-1,2-cyclohexanediamine](1,2,4,5-tetramethylbenzene) ruthenium, hydrido

[(R,R)-N-trifluoromethanesulfonyl-1,2-cyclohexanediamine](1,2,4,5-tetramethylbenzene) ruthenium, hydrido

[(S,S)-N-trifluoromethanesulfonyl-1,2-cyclohexanediamine](1,2,3,5-tetramethylbenzene) ruthenium, hydrido

[(R,R)-N-trifluoromethanesulfonyl-1,2-cyclohexanediamine](1,2,3,5-tetramethylbenzene) ruthenium, hydrido

[(S,S)-N-trifluoromethanesulfonyl-1,2-cyclohexanediamine](1,2,3,4-tetramethylbenzene) ruthenium, hydrido

[(R,R)-N-trifluoromethanesulfonyl-1,2-cyclohexanediamine](1,2,3,4-tetramethylbenzene) ruthenium, hydrido

[(S,S)-N-trifluoromethanesulfonyl-1,2-cyclohexanediamine](1,2,3,4,5-pentamethylbenzene) ruthenium, hydrido

[(R,R)-N-trifluoromethanesulfonyl-1,2-cyclohexanediamine](1,2,3,4,5-pentamethylbenzene) ruthenium, hydrido

[(S,S)-N-trifluoromethanesulfonyl-1,2-cyclohexanediamine](hexamethylbenzene) ruthenium, and hydrido

[(R,R)-N-trifluoromethanesulfonyl-1,2-cyclohexanediamine](hexamethylbenzene) ruthenium.

In an embodiment of the present invention, the optically active nitrogen-containing compound, the compound of a metal of group VIII of the periodic table, the base, and the compounds represented by general formulae (A) and (B) may be reacted by mixing. More preferably, the asymmetric metal complex is prepared beforehand from the optically active nitrogen-containing compound, the compound of a metal of group VIII of the periodic table, and the base, and the compounds represented by general formulae (A) and (B) are reacted by mixing in the presence of this asymmetric metal complex. By carrying out the preparation of the asymmetric metal complex in the presence of a hydrogen-donating compound an asymmetric metal hydrido complex is obtained, and by carrying it out in the absence of a hydrogen-donating compound an asymmetric metal amido complex is obtained. In the preparation of the asymmetric metal complex, the molar mixing ratio of the compound of a metal of group VIII of the periodic table and the optically active nitrogen-containing compound is 1.0:0.1 to 1.0:10.0, and it is preferable to mix molar equivalents of the metal and the optically active nitrogen-containing compound. The base is used at 0.1 to 100 molar equivalents relative to the compound of a metal of group VIII of the periodic table, and preferably 1.0 to 10 molar equivalents. As a catalyst for the asymmetric reaction, either the asymmetric metal amido complex or the asymmetric metal hydrido complex can be used. Methods for preparing an asymmetric metal complex are described in Angew. Chem., Int. Ed. Engl., 1997, 36, 285-288 and J. Org. Chem., 1999, 64, 2186-2187. Furthermore, the asymmetric metal hydrido complex or asymmetric metal amido complex prepared from the optically active nitrogen-containing compound, the compound of a metal of group VIII of the periodic table, and the base may be reacted with the compound represented by general formula (B) to give an asymmetric metal complex, which is then mixed and reacted as a catalyst with the compounds represented by general formulae (A) and (B) (Reference Example 2).

The reaction can be carried out in various types of solvent. Examples thereof include an aliphatic hydrocarbon such as pentane, hexane, cyclopentane, or cyclohexane, an aromatic compound such as toluene or xylene, a halogen compound such as dichloromethane, a ketone solvent such as acetone, methyl ethyl ketone, or cyclohexanone, an alcoholic solvent such as methanol, ethanol, 2-propanol, or 2-methyl-2-propanol, and an organic compound such as tetrahydrofuran, diethyl ether, dimethylsulfoxide (DMSO), dimethylformamide(DMF), or acetonitrile, and they may be used singly or in combination.

In the catalytic reaction, the concentrations of the compounds represented by general formulae (A) and (B) are from 0.01 mol/L of the above-mentioned solvent to a state in which no solvent is used, and preferably in the range of 0.1 to 3.0 mol/L. The amounts of the compounds represented by general formulae (A) and (B) relative to the asymmetric metal complex having the metal atom of group VIII of the periodic table are usually expressed as a molar ratio (S/C) of the reaction substrate relative to the asymmetric metal complex having the metal atom of group VIII of the periodic table, and S/C is in the range of 10 to 100,000, and preferably 50 to 2,000. The reaction temperature is on the order of −20° C. to 100° C. from the viewpoint of cost efficiency. More practically, the reaction can be carried out at around a room temperature of 20° C. to 40° C. The reaction time varies depending on the reaction conditions such as the reaction substrate concentration, the temperature, and the pressure, but the reaction is completed in a few minutes to 100 hours. The product can be purified by a known method such as column chromatography, distillation, or recrystallization.

EXAMPLES

The present invention is explained further in detail below with reference to Examples, but the present invention is not limited by the Examples. In the Examples, % ee denotes the percentage enantiomeric excess, and S/C denotes the molar ratio of the substrate to the catalyst (molar ratio of the substrate to ruthenium).

Furthermore, Tsdpen denotes N-(p-toluenesulfonyl)-1,2-diphenylethylenediamine and Msdpen denotes N-methanesulfonyl-1,2-diphenylethylenediamine.

Reference Example 1

Synthesis of the Asymmetric Ruthenium Amide Complex Ru[(S,S)-Tsdpen] (hexamethylbenzene)

Under an atmosphere of argon, 134 mg (0.2 mmol) of [RuCl$_2$(hexamethylbenzene)]$_2$, 147 mg (0.4 mmol) of (S,S)-TsDPEN, 183 mg (2.8 mmol) of potassium hydroxide, 3 mL of methylene chloride, and 3 mL of water were placed in a 20 mL Schlenk tube and stirred at room temperature for 1 hour. The organic phase was washed with water several times, and sodium sulfate was then added to the organic phase to dry it. The organic phase was further dried with CaH$_2$ and then filtered, the solvent was removed by distillation, and the residue was dried under vacuum. The violet crystals thus obtained were used directly in a reaction as a catalyst.

By the same procedure as in Reference Example 1, Ru[(S,S)-Tsdpen](1,2,3,4,5-pentamethylbenzene), Ru[(S,S)-Tsdpen](1,2,4,5-tetramethylbenzene), Ru[(S,S)-Tsdpen](1,3,5-trimethylbenzene), Ru[(S,S)-Tsdpen](p-cymene), and Ru[(S,S)-Msdpen](hexamethylbenzene) were synthesized. Furthermore, RuH[(R,R)-Tsdpen](1,3,5-trimethylbenzene) was synthesized by carrying out the reaction of Reference Example 1 in 2-propanol.

Example 1

Production of (R)-3-[bis(methoxycarbonyl)methyl]cyclohexanone

Under an atmosphere of argon, 12.6 mg (0.02 mmol, S/C=50) of Ru[(S,S)-Tsdpen] (hexamethylbenzene), 97 µL (1.0 mmol) of 2-cyclohexenone, 114 µL (1.0 mmol) of dimethyl malonate, and 1 mL of 2-methyl-2-propanol were placed in a 20 mL Schlenk tube and stirred at 30° C. for 48 hours. This solution was purified by flash column chromatography (hexane/acetone=90/10, SiO$_2$) to give 213 mg (93% yield) of the title compound. The optical purity was measured by HPLC (CHIRALPAK AS manufactured by Daicel Chemical Industries, Ltd., hexane: 2-propanol=85: 15, flow rate 0.5 mL/min, detection at 210 nm) and it was found to be 96% ee.

Example 2

Production of (S)-3-[bis(methoxycarbonyl)methyl]cyclohexanone

Under an atmosphere of argon, 24.0 mg (0.04 mmol, S/C=50) of RuH[(R,R)-Tsdpen] (1,3,5-trimethylbenzene), 194 µL (2.0 mmol) of 2-cyclohexenone, 229 µL (2.0 mmol) of dimethyl malonate, and 2 mL of acetone were placed in a 20 mL Schlenk tube and stirred at 30° C. for 48 hours. This solution was purified by flash column chromatography (hexane/acetone=90/10, SiO$_2$) to give 316 mg (69% yield) of the title compound. The optical purity was measured by HPLC (CHIRALPAK AS manufactured by Daicel Chemical Industries, Ltd., hexane:2-propanol=85:15, flow rate 0.5 mL/min, detection at 210 nm) and it was found to be 73% ee.

Example 3

Production of (S)-3-[bis(ethoxycarbonyl)methyl]cyclohexanone

Under an atmosphere of argon, 24.0 mg (0.04 mmol, S/C=50) of RuH[(R,R)-Tsdpen] (1,3,5-trimethylbenzene), 194 μL (2.0 mmol) of 2-cyclohexenone, 304 μL (2.0 mmol) of diethyl malonate, and 2 mL of acetone were placed in a 20 mL Schlenk tube and stirred at 30° C. for 48 hours. This solution was purified by flash column chromatography (hexane/acetone=90/10, SiO$_2$) to give 330 mg (64% yield) of the title compound. After this was converted into an ethylene ketal derivative as shown below, the optical purity was measured by HPLC (CHIRALCEL OD manufactured by Daicel Chemical Industries, Ltd., hexane: 2-propanol=97:3, flow rate 0.5 mL/min, detection at 210 nm) and it was found to be 77% ee.

[Chem. 30]

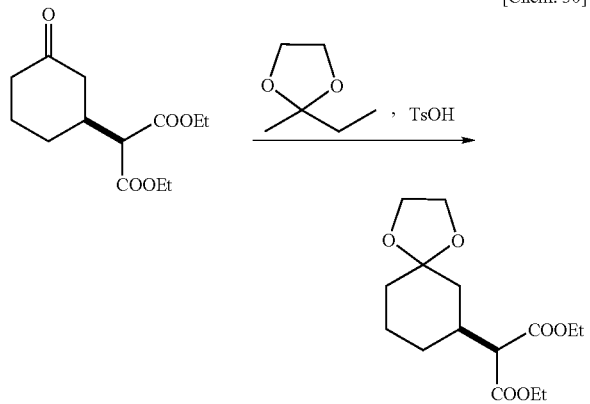

Example 4

Production of (R)-3-[bis(ethoxycarbonyl)methyl]cyclohexanone

Under an atmosphere of argon, 24.0 mg (0.04 mmol, S/C=50) of Ru[(S,S)-Tsdpen](p-cymene), 194 μL (2.0 mmol) of 2-cyclohexenone, 304 μL (2.0 mmol) of diethyl malonate, and 2 mL of 2-methyl-2-propanol were placed in a 20 mL Schlenk tube and stirred at 30° C. for 48 hours. This solution was purified by flash column chromatography (hexane/acetone=90/10, SiO$_2$) to give 409 mg (80% yield) of the title compound. After this was converted into an ethylene ketal derivative as shown in Example 3, the optical purity was measured by HPLC (CHIRALCEL OD manufactured by Daicel Chemical Industries, Ltd., hexane: 2-propanol=97:3, flow rate 0.5 mL/min, detection at 210 nm) and it was found to be 61% ee.

Example 5

Production of (R)-3-[bis(methoxycarbonyl)methyl]cyclopentanone

Under an atmosphere of argon, 12.6 mg (0.02 mmol, S/C=50) of Ru[(S,S)-Tsdpen](hexamethylbenzene), 84 μL (1.0 mmol) of 2-cyclopentenone, 114 μL (1.0 mmol) of dimethyl malonate, and 1 mL of 2-methyl-2-propanol were placed in a 20 mL Schlenk tube and stirred at 40° C. for 24 hours. This solution was purified by flash column chromatography (hexane/acetone=90/10, SiO$_2$) to give 210 mg (98% yield) of the title compound. The optical purity was measured by HPLC (CHIRALPAK AS manufactured by Daicel Chemical Industries, Ltd., hexane; 2-propanol=80:20, flow rate 1.0 mL/min, detection at 210 nm) and it was found to be 98% ee.

Example 6

Production of (R)-3-[bis(methoxycarbonyl)methyl]cyclopentanone

Under an atmosphere of argon, 11.0 mg (0.02 mmol, S/C=100) of Ru[(S,S)-Msdpen] (hexamethylbenzene), 168 μL (2.0 mmol) of 2-cyclopentenone, 228 μL (2.0 mmol) of dimethyl malonate, and 1 mL of 2-methyl-2-propanol were placed in a 20 mL Schlenk tube and stirred at 60° C. for 24 hours. This solution was purified by flash column chromatography (hexane/acetone=90/10, SiO$_2$) to give 422 mg (99% yield) of the title compound. The optical purity was measured by HPLC (CHIRALPAK AS manufactured by Daicel Chemical Industries, Ltd., hexane: 2-propanol=80:20, flow rate 1.0 mL/min, detection at 210 nm) and it was found to be 98% ee.

Example 7

Production of (S)-3-[bis(methoxycarbonyl)methyl]cyclopentanone

Under an atmosphere of argon, 12.0 mg (0.02 mmol, S/C=50) of RuH[(R,R)-Tsdpen] (1,3,5-trimethylbenzene), 84 μL (1.0 mmol) of 2-cyclopentenone, 114 μL (1.0 mmol) of dimethyl malonate, and 1 mL of acetone were placed in a 20 mL Schlenk tube and stirred at 40° C. for 24 hours. This solution was purified by flash column chromatography (hexane/acetone=90/10, SiO$_2$) to give 213 mg (99% yield) of the title compound. The optical purity was measured by HPLC (CHIRALPAK AS manufactured by Daicel Chemical Industries, Ltd., hexane:2-propanol=80:20, flow rate 1.0 mL/min, detection at 210 nm) and it was found to be 89% ee.

Example 8

Production of (R)-3-[bis(ethoxycarbonyl)methyl]cyclopentanone

Under an atmosphere of argon, 12.6 mg (0.02 mmol, S/C=50) of Ru[(S,S)-Tsdpen] (hexamethylbenzene), 84 μL (1.0 mmol) of 2-cyclopentenone, 152 μL (1.0 mol) of diethyl malonate, and 1 mL of 2-methyl-2-propanol were placed in a 20 mL Schlenk tube and stirred at 40° C. for 24 hours. This solution was purified by flash column chromatography (hexane/acetone=90/10, SiO$_2$) to give 233 mg (96% yield) of the title compound. After this was converted into an ethylene ketal derivative by the same procedure as in Example 3, the optical purity was measured by HPLC (CHIRALCEL OD manufactured by Daicel Chemical Industries, Ltd., hexane: 2-propanol=97:3, flow rate 0.5 mL/min, detection at 210 nm) and it was found to be 96% ee.

Example 9

Production of (S)-3-[bis(ethoxycarbonyl)methyl]cyclopentanone

Under an atmosphere of argon, 24.0 mg (0.04 mmol, S/C=50) of RuH[(R,R)-Tsdpen] (1,3,5-trimethylbenzene), 168 μL (2.0 mmol) of 2-cyclopentenone, 304 μL (2.0 mmol) of diethyl malonate, and 2 mL of acetone were placed in a 20 mL Schlenk tube and stirred at 40° C. for 24 hours. This solution was purified by flash column chromatography (hexane/acetone=90/10, SiO$_2$) to give 462 mg (95% yield) of the title compound. After this was converted into an ethylene ketal derivative by the same procedure as in Example 3, the optical purity was measured by HPLC (CHIRALCEL OD manufactured by Daicel Chemical Industries, Ltd., hexane: 2-propanol=97: 3, flow rate 0.5 mL/min, detection at 210 nm) and it was found to be 91% ee.

Example 10

Production of 3-[1,1-bis(methoxycarbonyl)ethyl]cyclopentanone

Under an atmosphere of argon, 12.6 mg (0.02 mmol, S/C=50) of Ru[(S,S)-Tsdpen] (hexamethylbenzene), 84 μL (1.0 mmol) of 2-cyclopentenone, 133 μL (1.0 mmol) of dimethyl methylmalonate, and 1 mL of 2-methyl-2-propanol were placed in a 20 mL Schlenk tube and stirred at 40° C. for 24 hours. This solution was purified by flash column chromatography (hexane/acetone=90/10, SiO$_2$) to give 54 mg (24% yield) of the title compound. The optical purity was measured by HPLC (CHIRALPAK AS manufactured by Daicel Chemical Industries, Ltd., hexane: 2-propanol=80:20, flowrate 1.5 mL/min, detection at 210 nm) and it was found to be 76% ee.

Example 11

Production of 3-[bis(methoxycarbonyl)methyl]-4, 4-dimethylcyclopentanone

Under an atmosphere of argon, 12.3 mg (0.02 mmol, SIC=50) of Ru[(S,S)-Tsdpen] (1,2,3,4,5-pentamethylbenzene), 122 μL (1.0 mmol) of 4,4-dimethyl-2-cyclopentenone, 114 μL (1.0 mmol) of dimethyl malonate, and 1 mL of 2-methyl-2-propanol were placed in a 20 mL Schlenk tube and stirred at 40° C. for 48 hours. This solution was purified by flash column chromatography (hexane/acetone=90/10, SiO$_2$) to give 141 mg (58% yield) of the title compound. After they were converted into an ethylene ketal derivative by the same procedure as in Example 3, the optical purity was measured by HPLC (CHIRALCEL OD manufactured by Daicel Chemical Industries, Ltd., hexane; 2-propanol=97:3, flow rate 0.5 mL/min, detection at 210 nm) and it was found to be 99% ee.

Example 12

Production of 3-[(acetyl) (methoxycarbonyl)methyl]cyclopentanone

Under an atmosphere of argon, 12.6 mg (0.02 mmol, S/C=50) of Ru[(S,S)-Tsdpen] (hexamethylbenzene), 84 μL (1.0 mmol) of 2-cyclopentenone, 108 μL (1.0 mmol) of methyl acetoacetate, and 1 mL of 2-methyl-2-propanol were placed in a 20 mL Schlenk tube and stirred at 40° C. for 24 hours. This solution was purified by flash column chromatography (hexane/acetone=90/10, SiO$_2$) to give 196 mg (99% yield) of the title compound. The percentage diastereomeric excess and the percentage enantiomeric excess were measured by $^1$H NMR and HPLC (CHIRALPAK AS manufactured by Daicel Chemical Industries, Ltd., hexane: 2-propanol=80:20, flow rate 1.0 mL/min, detection at 210 nm), it was found that the product was a 1:1 diastereomeric mixture and each diastereomer was present in 70% ee.

Example 13

Production of (R)-3-[bis(methoxycarbonyl)methyl]cyclopentanone

Under an atmosphere of argon, 11.0 mg (0.02 mmol, S/C=100) of Ru[(S,S)-Msdpen] (hexamethylbenzene), 168 μL (2.0 mmol) of 2-cyclopentenone, 228 μl (2.0 mmol) of dimethyl malonate, and 1 mL of 2-methyl-2-propanol were placed in a 20 mL Schlenk tube and stirred at 30° C. for 72 hours. This solution was purified by flash column chromatography (hexane/acetone=90/10, SiO$_2$) to give 425 mg (99% yield) of the title compound. The optical rotation $[\alpha]^{D21}$ was +96.3 (c 0.54, CHCl$_3$). The optical purity was measured by HPLC (CHIRALPAK AS manufactured by Daicel Chemical Industries, Ltd., hexane:2-propanol=80:20, flow rate 1.0 mL/min, detection at 210 nm) and it was found to be 98% ee.

Example 14

Production of (R)-3-[bis(methoxycarbonyl)methyl]cyclohexanone

Under an atmosphere of argon, 11.0 mg (0.02 mmol, S/C=100) of Ru[(S,S)-Msdpen] (hexamethylbenzene), 194 μL (2.0 mmol) of 2-cyclohexenone, 228 μL (2.0 mmol) of dimethyl malonate, and 1 mL of 2-methyl-2-propanol were placed in a 20 mL Schlenk tube and stirred at 30° C. for 72 hours. This solution was purified by flash column chromatography (hexane/acetone=90/10, SiO$_2$) to give 443 mg (97% yield) of the title compound. The optical rotation $[\alpha]^{D23}$ was +3.45 (c 2.44, CHCl$_3$). The optical purity was measured by HPLC (CHIRALPAK AS manufactured by Daicel Chemical Industries, Ltd., hexane:2-propanol=85:15, flow rate 0.5 mL/min, detection at 210 nm) and it was found to be 98% ee.

Example 15

Production of (R)-3-[bis(methoxycarbonyl)methyl]cycloheptanone

Under an atmosphere of argon, 11.0 mg (0.02 mmol, S/C=100) of Ru[(S,S)-Msdpen] (hexamethylbenzene), 111 μL (1.0 mmol) of 2-cycloheptenone, 114 μL (1.0 mmol) of dimethyl malonate, and 1 mL of 2-methyl-2-propanol were placed in a 20 mL Schlenk tube and stirred at 30° C. for 72 hours. This solution was purified by flash column chromatography (hexane/acetone=90/10, SiO$_2$) to give 181 mg (75% yield) of the title compound. The optical rotation $[\alpha]^{D27}$ was +45.2 (c 1.76, CHCl$_3$). This was reacted with (2R,3R)-butanediol in the presence of a catalytic amount of p-toluenesulfonic acid so as to be converted into a ketal derivative. The $^{13}$C NMR spectrum of this derivative was measured, and the optical purity was determined from the ratio of the integrals of the peaks of two diastereomers, with the result that it was >99% ee.

Example 16

Production of 3-[1,1-bis(methoxycarbonyl)ethyl]cyclopentanone

Under an atmosphere of argon, 11.0 mg (0.02 mmol, S/C=50) of Ru[(S,S)-Msdpen] (hexamethylbenzene), 84 μL (1.0 mmol) of 2-cyclopentenone, 133 μL (1.0 mmol) of dimethyl methylmalonate, and 1 mL of toluene were placed in a 20 mL Schlenk tube and stirred at 30° C. for 48 hours. This solution was purified by flash column chromatography (hexane/acetone=90/10, SiO$_2$) to give 116 mg (51% yield) of the title compound. The optical rotation $[\alpha]_D^{25}$ was +87.2(c 1.00, CHCl$_3$). The optical purity was measured by HPLC (CHIRALPAK AS manufactured by Daicel Chemical Industries, Ltd., hexane:2-propanol=80:20, flow rate 1.5 mL/min, detection at 210 nm) and it was found to be 97% ee.

Example 17

Production of 3-[bis(methoxycarbonyl)methyl]-4, 4-dimethylcyclopentanone

Under an atmosphere of argon, 11.0 mg (0.02 mmol, S/C=50) of Ru[(S,S)-Msdpen] (hexamethylbenzene), 122 µL (1.0 mmol) of 4,4-dimethyl-2-cyclopentenone, 114 µL (1.0 mmol) of dimethyl malonate, and 1 mL of 2-methyl-2-propanol were placed in a 20 mL Schlenk tube and stirred at 30° C. for 72 hours. This solution was purified by flash column chromatography (hexane/acetone=90/10, SiO$_2$) to give 202 mg (83% yield) of the title compound. The optical rotation $[\alpha]_D^{25}$ was +101.6 (c 1.04, CHCl$_3$). After this was converted into an ethylene ketal derivative by the same procedure as in Example 3, the optical purity was measured by HPLC (CHIRALCEL OD manufactured by Daicel Chemical Industries, Ltd., hexane: 2-propanol=97:3, flow rate 0.5 mL/min, detection at 210 nm) and it was found to be 99% ee.

Example 18

Production of 3-[(acetyl) (methoxycarbonyl)methyl]cyclopentanone

Under an atmosphere of argon, 12.6 mg (0.02 mmol, S/C=50) of Ru[(S,S)-Tsdpen] (hexamethylbenzene), 84 µL (1.0 mmol) of 2-cyclopentenone, 108 µL (1.0 mmol) of methyl acetoacetate, and 1 mL of dry toluene were placed in a 20 mL Schlenk tube and stirred at 40° C. for 24 hours. This solution was purified by flash column chromatography (hexane/acetone=90/10, SiO$_2$) to give 196 mg (99% yield) of the title compound. The optical rotation $[\alpha]_D^{25}$ was +83.5 (c 1.35, CHCl$_3$). The percentage diastereomeric excess and the percentage enantiomeric excess were measured by $^1$H NMR and HPLC (CHIRALCEL OD manufactured by Daicel Chemical Industries, Ltd., hexane:2-propanol=80:20, flow rate 1.0 mL/min, detection at 210 nm), and the results were that the product was a 1:1 diastereomeric mixture and each diastereomer was present in 91% ee.

Reference Example 2

Synthetic Method for the Asymmetric Ruthenium Malonate Complex Ru[CH$_2$(CO$_2$CH$_3$)$_2$][(R,R)-Tsdpen](mesitylene)

Under an atmosphere of argon, 50 mg (0.085 mmol) of RuH[(R,R)-Tsdpen](mesitylene), 78 µL (0.68 mmol) of dimethyl malonate, and 4 mL of dry acetone were placed in a 20 mL Schlenk tube and recrystallized without further treatment to give 24 mg (40% yield) of orange crystals. Since the complex so obtained rapidly dissociated in solution to give an amide complex and dimethyl malonate, the $^1$H NMR was measured at a low temperature (−30° C.) so that dissociation did not occur. $^1$H NMR (CD$_2$Cl$_2$) δ 2.06 (s, 9H), 2.20 (s, 3H), 3.55-3.80 (m, 7H), 3.88 (t, J=11.5 Hz, 1H), 4.09 (s, 1H), 4.27 (d, J=11.5 Hz, 1H), 5.06 (s, 3H), 6.65-7.35 (m, 15H)

This complex can also be used as a catalyst for a Michael reaction.

EFFECTS OF THE INVENTION

In accordance with the present invention, Michael addition products such as optically active ketones and esters having high optical purity can be obtained by a simple procedure in high yields.

What is claimed is:

1. A process for producing an optically active compound represented by general formula (C)

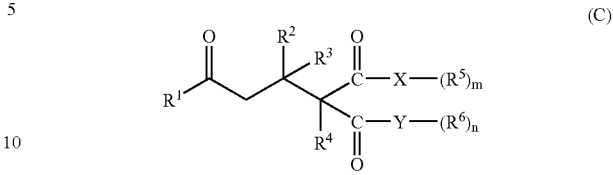

wherein R$^1$ denotes a saturated or unsaturated aliphatic hydrocarbon group or alicyclic hydrocarbon group, which may have a substituent, or a hydrogen atom, an alkoxy group, or an amino group; R$^2$ and R$^3$ independently denote a hydrogen atom, or a saturated or unsaturated aliphatic hydrocarbon group or alicyclic hydrocarbon group, which may have a substituent, and R$^1$ and R$^2$, R$^1$ and R$^3$, or R$^2$ and R$^3$ may be bonded to each other to form a ring, R$^4$ denotes a hydrogen atom, or a saturated or unsaturated aliphatic hydrocarbon group or alicyclic hydrocarbon group, which may have a substituent; R$^5$ and R$^6$ independently denote a saturated or unsaturated aliphatic hydrocarbon group or alicyclic hydrocarbon group, which may have a substituent, or a straight-chain or branched C1 to C20 alkoxy group, and R$^4$ and R$^5$, R$^4$ and R$^6$, or R$^5$ and R$^6$ may be bonded to each other to form a ring; X and Y independently denote a single bond, or an oxygen atom; and m and n are independently 1 or 2, by reacting a compound represented by general formula (A)

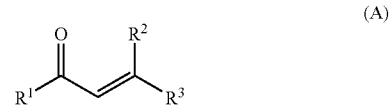

wherein R$^1$, R$^2$, and R$^3$ have the same meaning as above, and a compound represented by general formula (B)

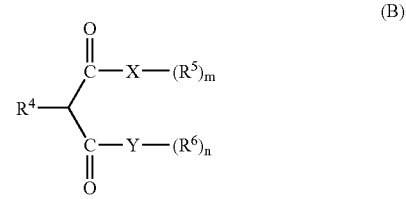

wherein R$^4$, R$^5$, R$^6$, X, Y, m, and n have the same meaning as above, with an asymmetric metal complex obtained from an optically active nitrogen-containing compound and a complex of a metal of group VIII of the periodic table; with the proviso that the substituent is not a heteromonocyclic or heteropolycyclic group.

2. The process for producing an optically active compound according to claim 1, wherein X and Y of compound (B) according to claim 1 are both oxygen atoms.

3. The process for producing an optically active compound according to claim 1, wherein X of compound (B) according to claim 1 is an oxygen atom and Y is a single bond, or X is a single bond and Y is an oxygen atom.

4. The process for producing an optically active compound according to claim 1, wherein the optically active nitrogen-containing compound has a structure represented by general formula (D)

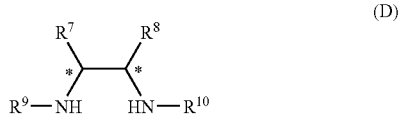
(D)

wherein $R^7$ and $R^8$ independently denote an aromatic monocyclic or aromatic polycyclic hydrocarbon group, which may have a substituent, and $R^7$ and $R^8$ may be bonded to each other to form a ring; $R^9$ denotes a hydrogen atom or an alkyl group; $R^{10}$ denotes an alkylsulfonyl group, or an arylsulfonyl group; and * denotes an asymmetric carbon atom; with the proviso that the substituent is not a heteromonocyclic or heteropolycyclic group.

5. The process for producing an optically active compound according to claim 1, wherein the asymmetric metal complex is an asymmetric ruthenium amido complex represented by general formula (E)

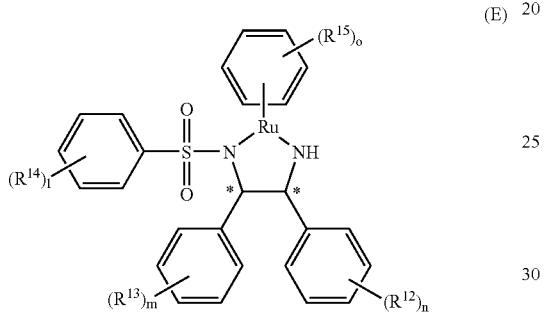
(E)

wherein $R^{12}$, $R^{13}$, and $R^{14}$, independently denote a hydrogen atom, an alkyl group, a halogen atom, or an alkoxy group, l independently denotes an integer of 1 to 5, and m and n have the same meaning as claim 1, $R^{15}$ denotes a methyl group, an ethyl group, a propyl group, or an isopropyl group, o denotes an integer of 0 to 6, and * denotes an asymmetric carbon atom.

6. The process for producing an optically active compound according to claim 1, wherein the asymmetric metal complex is an asymmetric ruthenium hydrido complex represented by general formula (F)

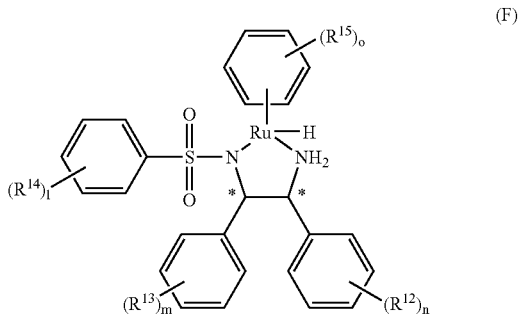
(F)

wherein $R^{12}$, $R^{13}$, $R^{14}$, $R^{15}$, l, m, n and o have the same meaning as claim 1, and * denotes an asymmetric carbon atom.

* * * * *